(12) United States Patent
Schaer

(10) Patent No.: US 7,881,807 B2
(45) Date of Patent: Feb. 1, 2011

(54) BALLOON ANCHOR WIRE

(76) Inventor: Alan K. Schaer, 5050 Elmgrove Ct., San Jose, CA (US) 95130

( * ) Notice: Subject to any disclaimer, the term of this patent is extended or adjusted under 35 U.S.C. 154(b) by 0 days.

(21) Appl. No.: 10/447,921

(22) Filed: May 29, 2003

(65) Prior Publication Data

US 2003/0195510 A1 Oct. 16, 2003

Related U.S. Application Data

(62) Division of application No. 09/569,735, filed on May 11, 2000, now Pat. No. 6,595,989.

(51) Int. Cl.
*A61N 1/00* (2006.01)
(52) U.S. Cl. .......................... 607/122; 128/898; 606/41; 606/47; 607/126
(58) Field of Classification Search ............ 606/4–506, 606/1, 41, 48–50; 607/107, 113, 122, 126; 128/898
See application file for complete search history.

(56) References Cited

U.S. PATENT DOCUMENTS

| | | | |
|---|---|---|---|
| 4,411,266 A | 10/1983 | Cosman | |
| 4,449,528 A | 5/1984 | Auth et al. | |
| 4,522,205 A | 6/1985 | Taylor et al. | |
| 4,569,801 A | 2/1986 | Molloy et al. | |
| 4,641,649 A | 2/1987 | Walinsky et al. | |
| 4,660,571 A | 4/1987 | Hess et al. | |
| 4,662,368 A | 5/1987 | Hussein et al. | |
| 4,672,962 A | 6/1987 | Hershenson | |
| 4,673,563 A | 6/1987 | Berne et al. | |
| 4,676,258 A | 6/1987 | Inokuchi et al. | |
| 4,790,311 A | 12/1988 | Ruiz | |
| 4,807,620 A | 2/1989 | Strul et al. | |
| 4,924,863 A | 5/1990 | Sterzer | |
| 4,936,281 A | 6/1990 | Stasz | |
| 4,940,064 A | 7/1990 | Desai | |
| 4,945,912 A | 8/1990 | Langberg | |
| 4,976,711 A | 12/1990 | Parins et al. | |
| 4,998,933 A | 3/1991 | Eggers et al. | |
| 5,035,694 A | 7/1991 | Kasprzyk et al. | |
| 5,078,717 A | 1/1992 | Parins et al. | |
| 5,078,736 A | 1/1992 | Behl | |
| 5,090,958 A | 2/1992 | Sahota | |
| 5,100,423 A | 3/1992 | Fearnot | |

(Continued)

FOREIGN PATENT DOCUMENTS

| | | |
|---|---|---|
| GB | 2208138 A | 3/1989 |
| WO | 93/00958 | 1/1993 |
| WO | 93/08755 | 5/1993 |
| WO | 93/16632 | 9/1993 |
| WO | 93/20767 | 10/1993 |
| WO | 93/20886 A1 | 10/1993 |
| WO | 94/21165 A1 | 9/1994 |
| WO | 94/21167 A | 9/1994 |

(Continued)

OTHER PUBLICATIONS

Avitall, B. et al. Physics and Engineering of Transcatheter Cardiac Tissue Ablation, JACC vol. 22(3):921-932 (1993).
Cox, JL et al. The Surgical Treatment of Atrial Fibrillation. I. Summary, Thoracic and Cardiovascular Surgery 101(3):402-405 (1991).
Cox, JL et al. The Surgical Treatment of Atrial Fibrillation. IV. Surgical Technique, Thoracic and Cardiovascular Surgery 101(4):584-592 (1991).

(Continued)

*Primary Examiner*—Michael Peffley
*Assistant Examiner*—Victoria W Chen

(57) ABSTRACT

The present invention relates to an anchor device comprising an elongated tubular body having an expandable member disposed on its distal end portion. The invention also relates to a system adapted to position and anchor the distal end of an ablation device at a location where a pulmonary vein extends from the atrium.

2 Claims, 11 Drawing Sheets

U.S. PATENT DOCUMENTS

| | | |
|---|---|---|
| 5,104,393 A | 4/1992 | Isner et al. |
| 5,147,355 A | 9/1992 | Friedman et al. |
| 5,167,239 A | 12/1992 | Cohen et al. |
| 5,178,618 A | 1/1993 | Kandarpa |
| 5,207,229 A | 5/1993 | Winters et al. |
| 5,226,430 A | 7/1993 | Spears et al. |
| 5,228,442 A | 7/1993 | Imran |
| 5,231,994 A | 8/1993 | Harmjanz |
| 5,231,995 A | 8/1993 | Desai |
| 5,255,679 A | 10/1993 | Imran |
| 5,263,493 A | 11/1993 | Avitall |
| 5,292,321 A | 3/1994 | Lee |
| 5,293,869 A | 3/1994 | Edwards et al. |
| 5,295,484 A | 3/1994 | Marcus et al. |
| 5,313,943 A | 5/1994 | Houser et al. |
| 5,324,255 A | 6/1994 | Passafaro et al. |
| 5,324,284 A | 6/1994 | Imran |
| 5,341,807 A | 8/1994 | Nardella |
| 5,342,292 A | 8/1994 | Nita et al. |
| 5,344,435 A | 9/1994 | Turner et al. |
| 5,345,936 A | 9/1994 | Pomeranz et al. |
| 5,348,554 A | 9/1994 | Imran et al. |
| 5,364,376 A | 11/1994 | Horzewski |
| 5,368,558 A | 11/1994 | Nita |
| 5,370,678 A | 12/1994 | Edwards et al. |
| 5,385,148 A | 1/1995 | Lesh et al. |
| 5,385,544 A | 1/1995 | Edwards et al. |
| 5,391,197 A | 2/1995 | Burdette et al. |
| 5,409,000 A | 4/1995 | Imran |
| 5,423,808 A | 6/1995 | Edwards et al. |
| 5,423,811 A | 6/1995 | Imran et al. |
| 5,427,119 A | 6/1995 | Swartz et al. |
| 5,433,708 A | 7/1995 | Nichols et al. |
| 5,449,380 A | 9/1995 | Chin |
| 5,456,682 A | 10/1995 | Edwards et al. |
| 5,474,530 A | 12/1995 | Passafaro et al. |
| 5,484,400 A | 1/1996 | Edwards et al. |
| 5,487,385 A | 1/1996 | Avitall |
| 5,497,199 A | 3/1996 | Asada et al. |
| 5,497,774 A | 3/1996 | Swartz et al. |
| 5,505,702 A | 4/1996 | Arney |
| 5,505,730 A | 4/1996 | Edwards |
| 5,522,873 A | 6/1996 | Jackman et al. |
| 5,545,161 A | 8/1996 | Imran |
| 5,545,193 A | 8/1996 | Fleischman et al. |
| 5,549,661 A | 8/1996 | Kordis et al. |
| 5,558,720 A | 9/1996 | Sarraf et al. |
| 5,562,720 A | 10/1996 | Stern et al. |
| 5,564,440 A | 10/1996 | Swartz et al. |
| 5,571,088 A | 11/1996 | Lennox et al. |
| 5,575,766 A | 11/1996 | Swartz et al. |
| 5,575,772 A | 11/1996 | Lennox |
| 5,575,788 A | 11/1996 | Baker et al. |
| 5,575,801 A | 11/1996 | Habermeyer et al. |
| 5,575,810 A | 11/1996 | Swanson et al. |
| 5,582,609 A | 12/1996 | Swanson et al. |
| 5,588,432 A | 12/1996 | Crowley |
| 5,592,609 A | 1/1997 | Suzuki et al. |
| 5,606,974 A | 3/1997 | Castellano et al. |
| 5,607,422 A | 3/1997 | Smeets et al. |
| 5,617,854 A * | 4/1997 | Munsif ........................ 600/374 |
| 5,620,479 A | 4/1997 | Diederich |
| 5,630,837 A | 5/1997 | Crowley |
| 5,645,082 A | 7/1997 | Sung et al. |
| 5,658,278 A | 8/1997 | Imran et al. |
| 5,673,695 A | 10/1997 | McGee et al. |
| 5,676,662 A | 10/1997 | Fleischhacker et al. |
| 5,683,445 A | 11/1997 | Swoyer |
| 5,685,322 A | 11/1997 | Sung et al. |
| 5,685,839 A | 11/1997 | Edwards et al. |
| 5,687,723 A * | 11/1997 | Avitall ........................ 600/374 |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,702,438 A | 12/1997 | Avitall |
| 5,715,818 A | 2/1998 | Swartz et al. |
| 5,716,389 A | 2/1998 | Walinsky et al. |
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Larnard |
| 5,722,400 A | 3/1998 | Ockuly et al. |
| 5,722,401 A | 3/1998 | Pietroski et al. |
| 5,722,403 A | 3/1998 | McGee et al. |
| 5,722,963 A | 3/1998 | Lurie et al. |
| 5,725,494 A | 3/1998 | Brisken |
| 5,725,512 A | 3/1998 | Swartz et al. |
| 5,730,127 A | 3/1998 | Avitall |
| 5,730,704 A | 3/1998 | Avitall |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,755,663 A | 5/1998 | Larsen et al. |
| 5,755,664 A | 5/1998 | Rubenstein |
| 5,755,760 A | 5/1998 | Maguire et al. |
| 5,757,715 A | 5/1998 | Williams et al. |
| 5,769,846 A | 6/1998 | Edwards et al. |
| 5,782,239 A | 7/1998 | Webster, Jr. |
| RE35,880 E | 8/1998 | Waldman et al. |
| 5,797,877 A | 8/1998 | Hamilton et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,429 A | 9/1998 | Edwards |
| 5,807,249 A | 9/1998 | Qin et al. |
| 5,807,308 A | 9/1998 | Edwards |
| 5,807,391 A | 9/1998 | Wijkamp |
| 5,840,031 A | 11/1998 | Crowley |
| 5,840,076 A | 11/1998 | Swanson et al. |
| 5,842,984 A * | 12/1998 | Avitall ........................ 600/374 |
| 5,843,154 A | 12/1998 | Osypka |
| 5,846,218 A | 12/1998 | Brisken et al. |
| 5,860,920 A | 1/1999 | McGee et al. |
| 5,860,974 A | 1/1999 | Abele |
| 5,861,021 A | 1/1999 | Thome et al. |
| 5,971,983 A * | 10/1999 | Lesh ........................... 606/41 |
| 6,012,457 A * | 1/2000 | Lesh ........................... 128/898 |
| 6,024,740 A | 2/2000 | Lesh et al. |
| 6,033,397 A * | 3/2000 | Laufer et al. .................. 606/27 |
| 6,064,902 A | 5/2000 | Haissaguerre et al. |
| 6,071,279 A | 6/2000 | Whayne et al. |
| 6,071,281 A | 6/2000 | Burnside et al. |
| 6,117,101 A | 9/2000 | Diederich et al. |
| 6,164,283 A | 12/2000 | Lesh |
| 6,237,605 B1 * | 5/2001 | Vaska et al. .................. 128/898 |
| 6,325,797 B1 | 12/2001 | Stewart et al. ................ 606/41 |
| 6,488,637 B1 * | 12/2002 | Eder et al. .................... 600/585 |
| 6,490,474 B1 * | 12/2002 | Willis et al. .................. 600/424 |
| 6,522,930 B1 | 2/2003 | Schaer et al. |

| | | | |
|---|---|---|---|
| 6,652,517 B1 * | 11/2003 | Hall et al. | 606/41 |

FOREIGN PATENT DOCUMENTS

| | | | |
|---|---|---|---|
| WO | 95/10318 A | 4/1995 | |
| WO | 95/10319 A | 4/1995 | |
| WO | 95/10321 A | 4/1995 | |
| WO | 96/00036 A | 1/1996 | |
| WO | 96/10961 A1 | 4/1996 | |
| WO | 96/26675 A1 | 9/1996 | |
| WO | 96/32885 A | 10/1996 | |
| WO | 96/32897 A | 10/1996 | |
| WO | 97/32525 A | 9/1997 | |
| WO | 97/37607 A2 | 10/1997 | |
| WO | WO 97/37607 | 10/1997 | |
| WO | 97/45156 A | 12/1997 | |
| WO | 98/02201 A | 1/1998 | |
| WO | 98/14220 A | 4/1998 | |
| WO | 98/26724 A | 6/1998 | |
| WO | WO 98/49957 | 11/1998 | |
| WO | 99/00064 A | 1/1999 | |
| WO | WO 99/44519 | 1/1999 | |
| WO | WO 99/02096 | 11/1999 | |
| WO | WO 00/67830 | 11/2000 | |

OTHER PUBLICATIONS

Haisaguerre M. et al. Right and Left Atrial Radiofrequency Catheter Therapy of Paroxysmal Atrial Fibrillation, J Cardiovasc Electrophysiol. vol. 7, pp. 1132-1144, Dec. 1996.

Jais, P. et al. A Focal Source of Atrial Fibrillation Treated by Discrete Radiofrequency Ablation, Circulation 95(3):572-576 (1997).

Lesh, MD. Interventional Electrophysiology—State of the Art 1993, American Heart Journal, 126:686-698 (1993).

Sueda T et al. Simple Left Atrial Procedure for Chronic Atrial Fibrillation Associated With Mitral Valve Disease, the Society of Thoracic Surgeons 62:1796-1800 (1996).

Borbola, J. "Transcatheter Laser Ablation of Atrioventricular Nodal Reentrant tachycardia—Do We Really Need a Newer Energy Source?" European Heart Journal, vol. 18, pp. 357-358, 1997.

Diederich et al. "Introduction of Hyperthermia using an Intracavitary Multielement Ultrasonic Applicator." IEEE Transactions in Biomedical Engineering, vol. 36, No. 4, Apr. 1989.

Diederich et al. "The Development of Intracavitary Ultrasonic Applicators for Hyperthermia: A Design and Experimental Study", IEEE Medical Physics, 17 (4), pp. 626-634 Jul./Aug. 1990.

Fram et al. "Feasibility of Radiofrequency Powered, Thermal Balloon Ablation of Atrioventricular Bypass Tracts via the Coronary Sinus: In Vivo Canine Studies", Pace, vol. 18, pp. 1518-1530, Aug. 1995.

Hindricks et al. "IX Nonpharmacologic Management Catheter Ablation", Current Management of Arrythmias, pp. 373-378.

Jais, et al. "Biatrial Dimensions Relevant to Catheter Ablation", NASPE 17$^{th}$ Annual Scientific Sessions Abstract, Dec. 1995 Abstract.

Schuger et al. "Long Term Effects of Percutaneous Laser Balloon Ablation from the Canine Coronary Sinus", Circulation, vol. 86, No. 3, pp. 947-954, Sept. 1992.

Weber et al. "Laser Catheter coagulation of Atrial Myocardium for Ablation of Atrioventricular Nodal Recentrant Tachycardia" European Heart Journal, vol. 18, pp. 487-495, 1997.

Weber et al. "Laser Versus Radiofrequency Catheter Ablation of Ventricular Myocardium in Dogs: A comparative Test", Cardiology, 88: 346-352, 1997.

Weber et al. "Percutaneous Nd:YAG Laser coagulation of Ventricular Myocardium in dogs Using a Special Electrode Laser Catheter", PACE vol. 12, pp. 899-910, Jun. 1989.

Weber et al. "Transcatheter Endomyocardial Laser Revascularization: A Feasibility Test", The Thoracic and Cardiovascular Surgeon, vol. 46, pp. 74-76, Apr. 1998.

Weber et al. "Cardiovascular Application of the Nd: YAG Laser", Laser in Medicine and Surgery, 2:54-58, Mar. 8, 1988.

* cited by examiner

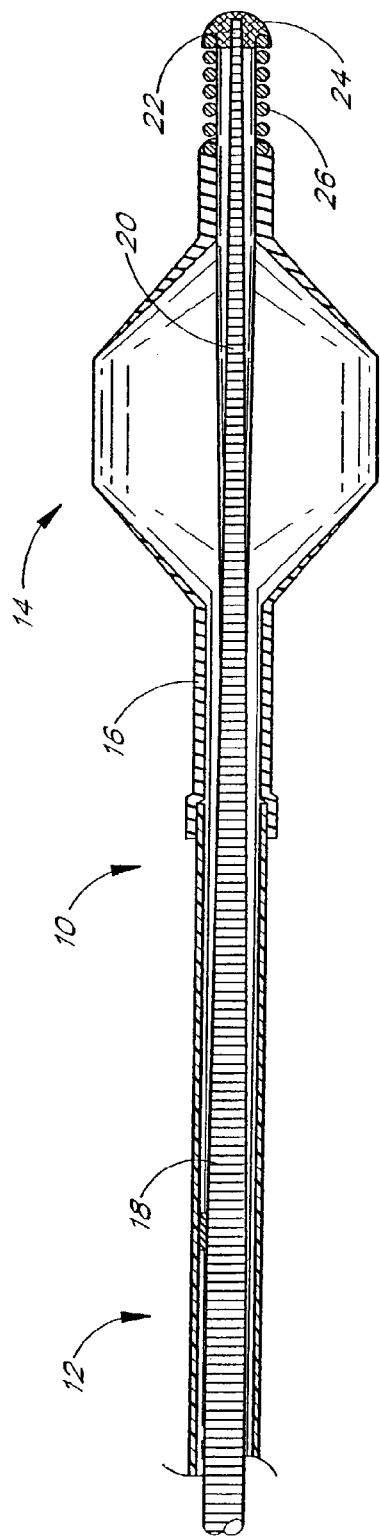
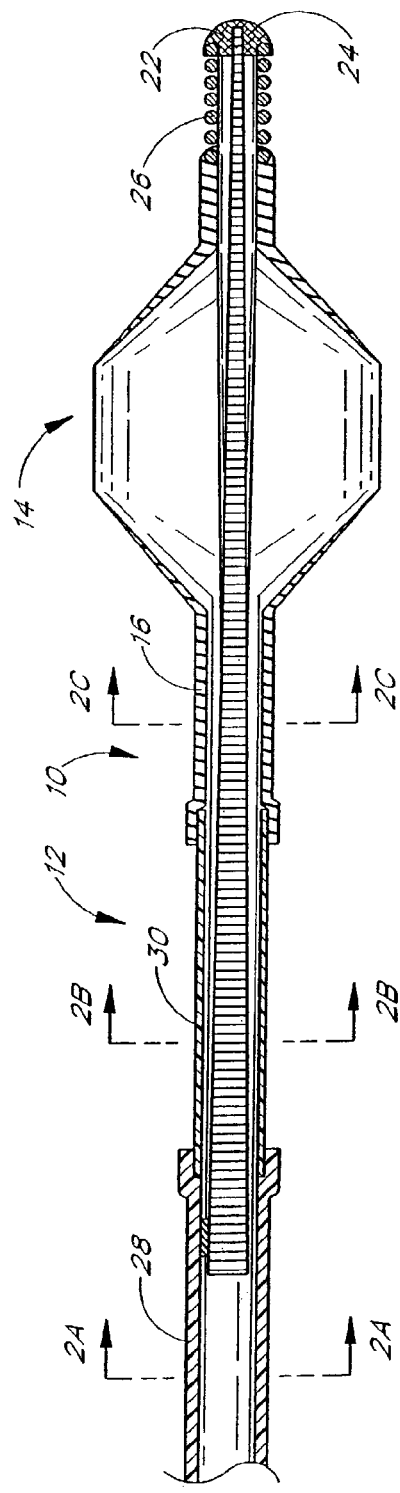
FIG. 1A
FIG. 1B

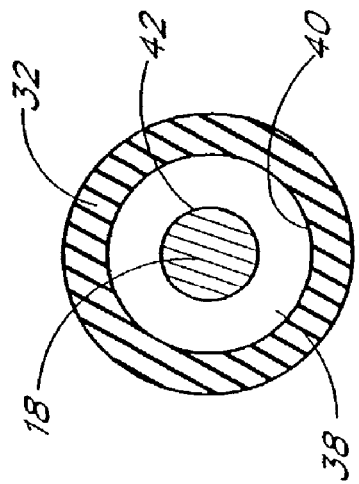
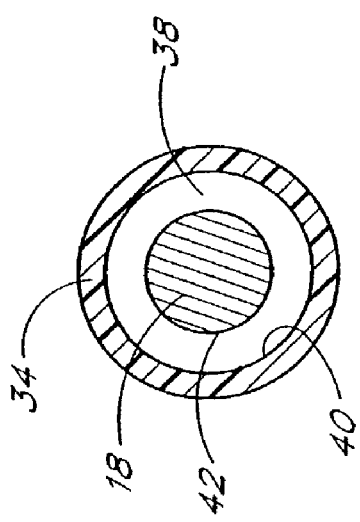
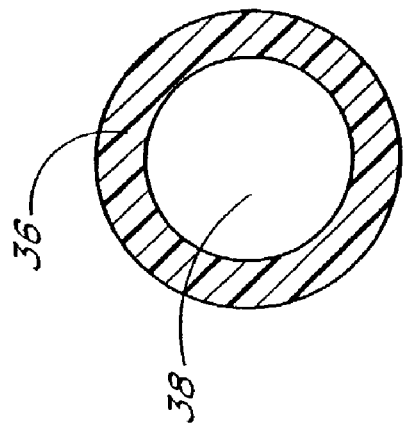
FIG. 2C
FIG. 2B
FIG. 2A

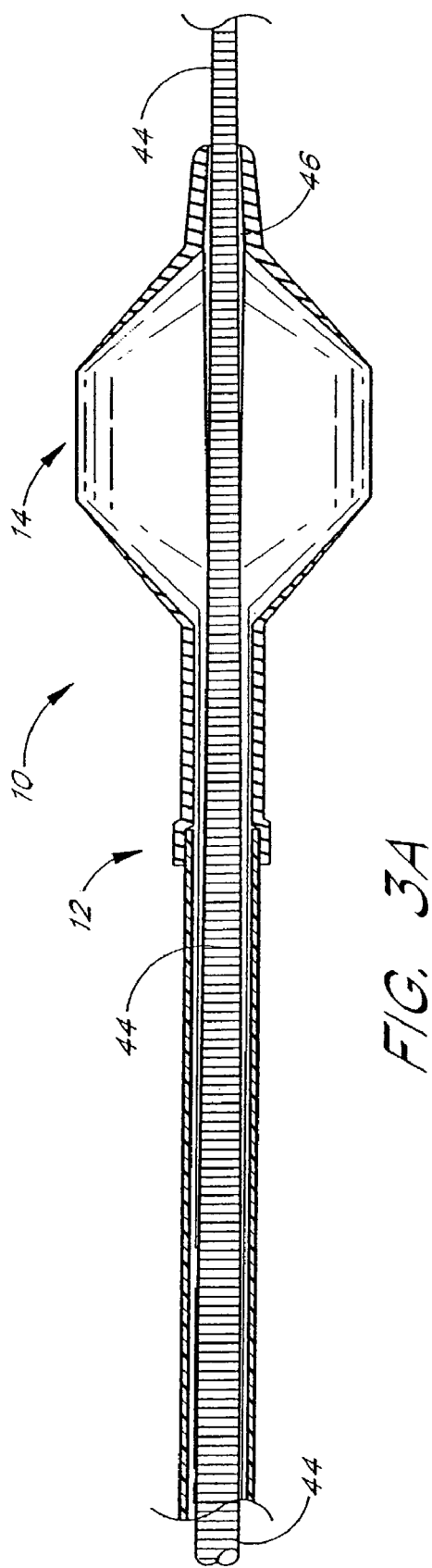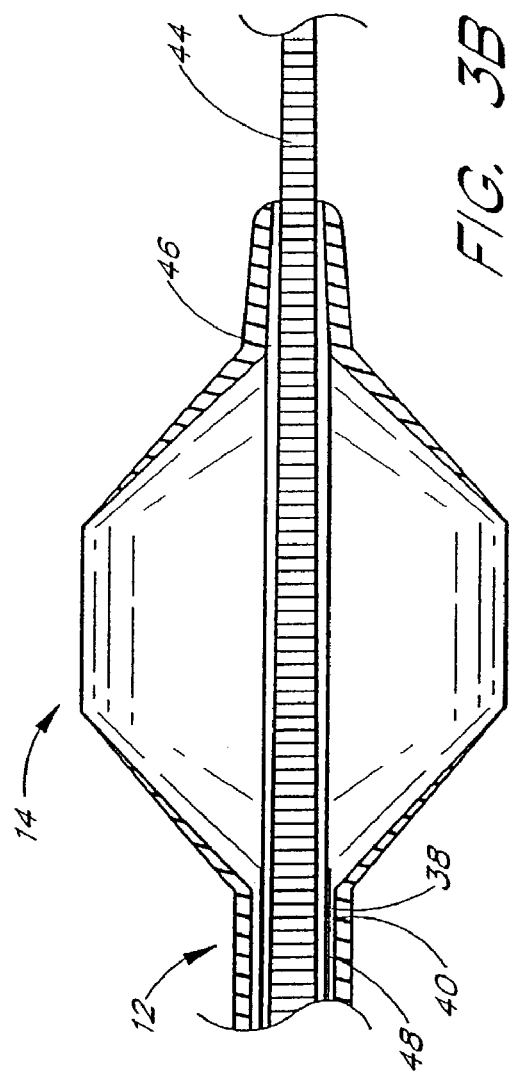

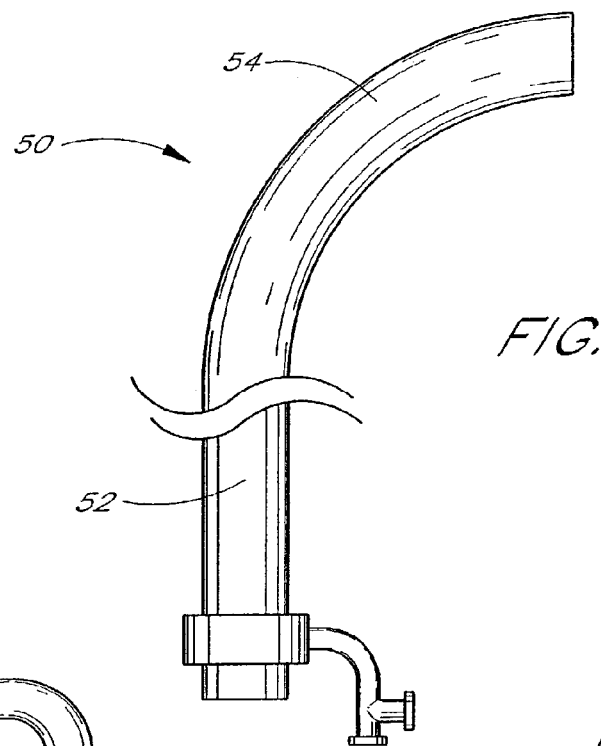
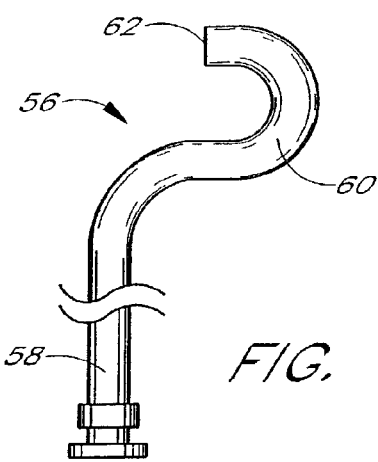
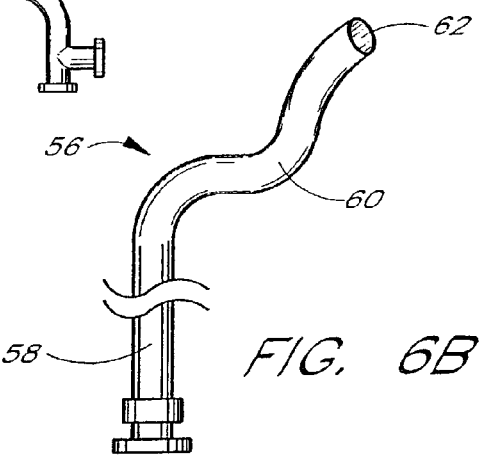
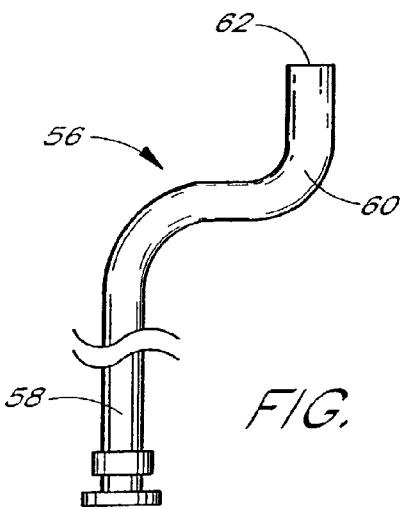
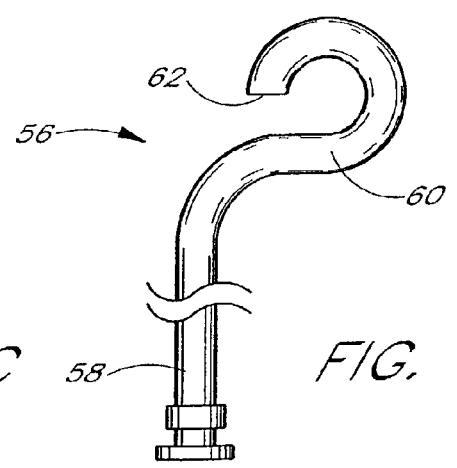
FIG. 5
FIG. 6A
FIG. 6B
FIG. 6C
FIG. 6D

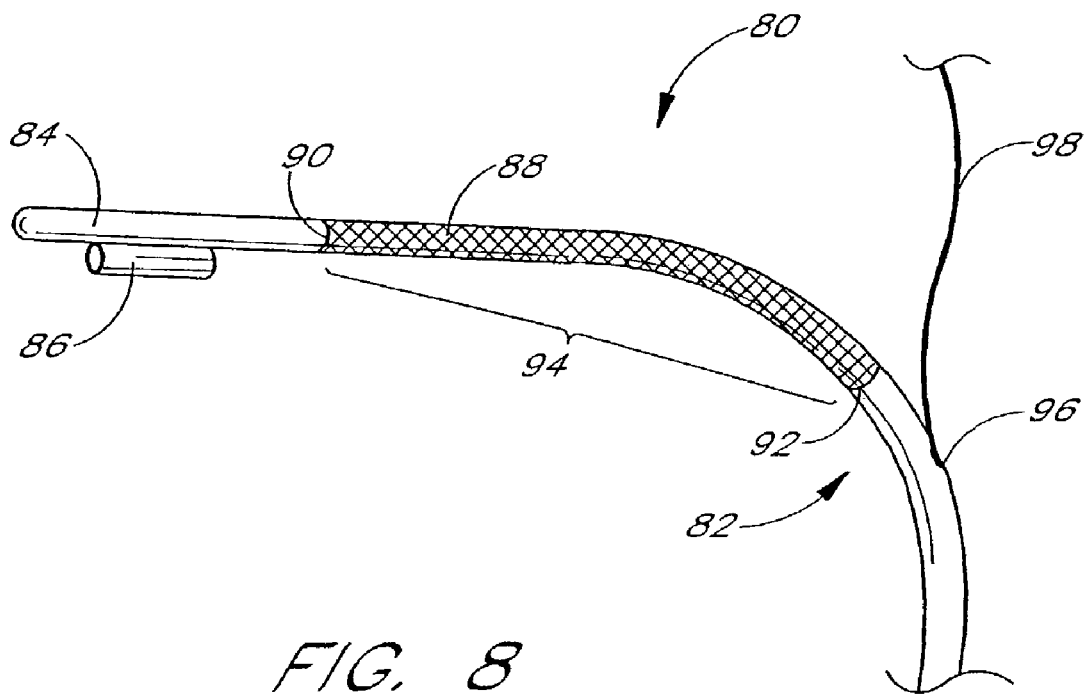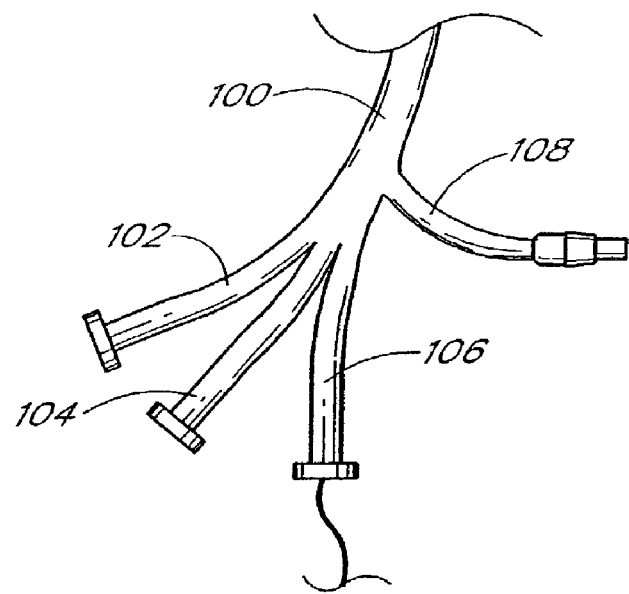
FIG. 8

BALLOON ANCHOR WIRE

RELATED APPLICATIONS

This application is a divisional of U.S. application Ser. No. 09/569,735 filed on May 11, 2000, now U.S. Pat. No. 6,595,989 and claims priority thereto under 35 U.S.C. §120 and 121.

BACKGROUND OF THE INVENTION

1. Field of the Invention

The present invention relates to a medical device and more specifically, to a anchor device which is adapted to facilitate the positioning of an ablation element at a location where a pulmonary vein extends from the left atrial wall.

2. Description of the Related Art

Cardiac arrhythmia's, particularly atrial fibrillation, are a pervasive problem in modern society. Although many individuals lead relatively normal lives despite persistent atrial fibrillation, the condition is associated with an increased risk of myocardial ischemia, especially during strenuous activity. Furthermore, persistent atrial fibrillation has been linked to congestive heart failure, stroke, and other thromboembolic events. Thus, atrial fibrillation is a major public health problem.

Normal cardiac rhythm is maintained by a cluster of pacemaker cells, known as the sinoatrial ("SA") node, located within the wall of the right atrium. The SA node undergoes repetitive cycles of membrane depolarization and repolarization, thereby generating a continuous stream of electrical impulses, called "action potentials." These action potentials orchestrate the regular contraction and relaxation of the cardiac muscle cells throughout the heart. Action potentials spread rapidly from cell to cell through both the right and left atria via gap junctions between the cardiac muscle cells. Atrial arrhythmia's result when electrical impulses originating from sites other than the SA node are conducted through the atrial cardiac tissue.

In most cases, atrial fibrillation results from perpetually wandering reentrant wavelets, which exhibit no consistent localized region(s) of aberrant conduction. Alternatively, atrial fibrillation may be focal in nature, resulting from rapid and repetitive changes in membrane potential originating from isolated centers, or foci, within the atrial cardiac muscle tissue. These foci exhibit consistent centrifugal patterns of electrical activation, and may act as either a trigger of atrial fibrillatory paroxysmal or may even sustain the fibrillation. Recent studies have suggested that focal arrhythmia's often originate from a tissue region along the pulmonary veins of the left atrium, and even more particularly in the superior pulmonary veins.

Several surgical approaches have been developed for the treatment of atrial fibrillation. For example, Cox, J L et al. disclose the "maze" procedure, in "The Surgical Treatment Of Atrial Fibrillation. I. Summary", *Thoracic and Cardiovascular Surgery* 101(3):402-405 (1991) and "The Surgical Treatment Of Atrial Fibrillation. IV. Surgical Technique", *Thoracic and Cardiovascular Surgery* 101(4):584-592 (1991). In general, the maze procedure is designed to relieve atrial arrhythmia by restoring effective SA node control through a prescribed pattern of incisions about the cardiac tissue wall. Although early clinical studies on the maze procedure included surgical incisions in both the right and left atrial chambers, more recent reports suggest that the maze procedure may be effective when performed only in the left atrium (see for example Sueda et al., "Simple Left Atrial Procedure For Chronic Atrial Fibrillation Associated With Mitral Valve Disease" (1996)).

The left atrial maze procedure involves forming vertical incisions from the two superior pulmonary veins and terminating in the region of the mitral valve annulus, traversing the inferior pulmonary veins en route. An additional horizontal incision connects the superior ends of the two vertical incisions. Thus, the atrial wall region bordered by the pulmonary vein ostia is isolated from the other atrial tissue. In this process, the mechanical sectioning of atrial tissue eliminates the atrial arrhythmia by blocking conduction of the aberrant action potentials.

The moderate success observed with the maze procedure and other surgical segmentation procedures have validated the principle that mechanically isolating cardiac tissue may successfully prevent atrial arrhythmia's, particularly atrial fibrillation, resulting from either perpetually wandering reentrant wavelets or focal regions of aberrant conduction. Unfortunately, the highly invasive nature of such procedures may be prohibitive in many cases. Consequently, less invasive catheter-based approaches to treat atrial fibrillation through cardiac tissue ablation have been developed.

These less invasive catheter-based therapies generally involve introducing a catheter within a cardiac chamber, such as in a percutaneous translumenal procedure, wherein an energy sink on the catheter's distal end portion is positioned at or adjacent to the aberrant conductive tissue. Upon application of energy, the targeted tissue is ablated and rendered non-conductive.

The catheter-based methods can be subdivided into two related categories, based on the etiology of the atrial arrhythmia. First, focal arrhythmias have proven amenable to localized ablation techniques, which target the foci of aberrant electrical activity. Accordingly, devices and techniques have been disclosed which use end-electrode catheter designs for ablating focal arrhythmia's centered in the pulmonary veins, using a point source of energy to ablate the locus of abnormal electrical activity. Such procedures typically employ incremental application of electrical energy to the tissue to form focal lesions.

The second category of catheter-based ablation methods is designed for treatment of the more common forms of atrial fibrillation, resulting from perpetually wandering reentrant wavelets. Such arrhythmias are generally not amenable to localized ablation techniques, because the excitation waves may circumnavigate a focal lesion. Thus, the second class of catheter-based approaches have generally attempted to mimic the earlier surgical segmentation techniques, such as the maze procedure, wherein continuous linear lesions are required to completely segment the atrial tissue so as to block conduction of the reentrant wave fronts.

For the purpose of comparison, ablation catheter devices and related methods have also been disclosed for the treatment of ventricular or supraventricular tachycardias, such as disclosed by Lesh, M D in "Interventional Electrophysiology—State Of The Art, 1993" *American Heart Journal*, 126: 686-698 (1993) and U.S. Pat. No. 5,231,995 to Desai.

An example of an ablation method targeting focal arrhythmia's originating from a pulmonary vein is disclosed by Haissaguerre et al. in "Right And Left Atrial Radiofrequency Catheter Therapy Of Paroxysmal Atrial Fibrillation" in *J. Cardiovasc. Electrophys.* 7(12):1132-1144 (1996). Haissaguerre et al. describe radiofrequency catheter ablation of drug-refractory paroxysmal atrial fibrillation using linear atrial lesions complemented by focal ablation targeted at arrhythmogenic foci in a screened patient population. The site of the arrhythmogenic foci was generally located just inside the superior pulmonary vein, and was ablated using a standard 4 mm tip single ablation electrode.

Another ablation method directed at paroxysmal arrhythmia's arising from a focal source is disclosed by Jais et al. "A Focal Source Of Atrial Fibrillation Treated By Discrete Radiofrequency Ablation" *Circulation* 95:572-576 (1997). At the site of arrhythmogenic tissue, in both right and left atria, several pulses of a discrete source of radiofrequency energy were applied in order to eliminate the fibrillatory process.

Application of catheter-based ablation techniques for treatment of reentrant wavelet arrhythmia's demanded development of methods and devices for generating continuous linear lesions, like those employed in the maze procedure. Initially, conventional ablation tip electrodes were adapted for use in "drag burn" procedures to form linear lesions. During the "drag" procedure, as energy was being applied, the catheter tip was drawn across the tissue along a predetermined pathway within the heart. Alternatively, sequentially positioning the distal tip electrode, applying a pulse of energy, and then re-positioning the electrode along a predetermined linear pathway also made lines of ablation.

Subsequently, conventional catheters were modified to include multiple electrode arrangements. Such catheters typically contained a plurality of ring electrodes circling the catheter at various distances extending proximally from the distal tip of the catheter. More detailed examples of such catheter-based tissue ablation assemblies have been disclosed in U.S. Pat. No. 5,676,662 to Fleischhacker et al.; U.S. Pat. No. 5,688,267 to Panescu et al.; and U.S. Pat. No. 5,693,078 to Desai et al.

Examples of catheter-based cardiac chamber segmentation procedures, particularly in the treatment of Wolff-Parkinson-White syndrome, are disclosed by Avitall et al. "Physics And Engineering Of Transcatheter Tissue Ablation" *J. Am. College of Cardiology*, 22(3):921-932 (1993) and Haissaguerre et al. "Right And Left Atrial Radiofrequency Catheter Therapy Of Paroxysmal Atrial Fibrillation" *J. Cardiovasc. Electrophys.* 7(12):1132-1144 (1996).

Further more detailed examples of transcatheter-based tissue ablation assemblies and methods are described in the following references: U.S. Pat. No. 5,575,810 to Swanson et al.; PCT Published Application WO 96/10961 to Fleischman et al.; U.S. Pat. No. 5,702,438 to Avitall; U.S. Pat. No. 5,687,723 to Avitall; U.S. Pat. No. 5,487,385 to Avitall; and PCT Published Application WO 97/37607 to Schaer.

While the disclosures above describe feasible catheter designs for imparting linear ablation tracks, as a practical matter, most of these catheter assemblies have been difficult to position and maintain placement and contact pressure long enough and in a sufficiently precise manner in the beating heart to successfully form segmented linear lesions along a chamber wall. Indeed, many of the aforementioned methods have generally failed to produce closed transmural lesions, thus leaving the opportunity for the reentrant circuits to reappear in the gaps remaining between point or drag ablations. In addition, minimal means have been disclosed in these embodiments for steering the catheters to anatomic sites of interest such as the pulmonary veins. Subsequently, a number of attempts to solve the problems encountered with precise positioning, maintenance of contact pressure, and catheter steering have been described. These include primarily the use of (1) preshaped ablating configurations, (2) deflectable catheter assemblies, and (3) transcatheter ablation assemblies.

None of the catheter-based ablation assemblies have included a balloon anchor wire for positioning and anchoring one end of an elongated ablation member within the ostium of a pulmonary vein. Nor does the prior art disclose a method for securing the ablation member between a first and second anchor, thereby maintaining a desired linear position in contact with the atrial wall and facilitating the formation of a linear ablation track along the length of tissue between the anchors.

SUMMARY OF THE INVENTION

The present invention relates to a tissue ablation system for ablating a region of tissue at the location where a pulmonary vein extends from an atrium in a patient. The tissue ablation system includes an anchor device adapted to be positioned within the pulmonary vein and an ablation device. The anchor device has an elongate body with a proximal end portion and a distal end portion. It also has an expandable member along the distal end portion that is adjustable between a radially collapsed condition and a radially expanded condition that is adapted to engage the pulmonary vein. The ablation device comprises an elongate catheter having a proximal region and a distal region. The ablation device has an ablation element located along the distal region, wherein the ablation device is adapted to slideably engage and track over the anchor device. By advancing the ablation device distally over the anchor device, which is positioned in the pulmonary vein, the ablation element can be positioned at the region of tissue to be ablated.

In one preferred mode of the tissue ablation system, the expandable member is an inflatable balloon. The elongate body may also comprise an inflation lumen, a pressurizable fluid source and a removable adapter on the proximal end portion of the elongate body. The adapter is adapted to couple the pressurizable fluid source to the inflation lumen. The balloon has an outer diameter of from about 0.114" to about 0.122" when inflated. The balloon may be made from any low density polymers or copolymers known in the art, such as polyethylene, polypropylene, polyolefins, PET, nylon, urethane, silicon, or Cflex. The polymeric material is preferably an irradiated linear low-density polyethylene.

In accordance with another variation, the anchor device of the tissue ablation system may have a shaped distal tip distal of the expandable member. Preferably, the anchor device is torquable and steerable, such that the anchor device may be directed into the pulmonary vein by manipulation of the proximal end portion. The elongate body of the anchor device comprises a polymeric tube.

The elongate body of the anchor device may be more flexible in the distal end portion than the proximal end portion. Also, the elongate body may have an intermediate region between the distal and proximal end portions, wherein the wall thickness of the proximal end portion is greater than the wall thickness of the intermediate region, such that the proximal end portion possess sufficient push force and kink resistance.

In one preferred mode, the anchor device also comprises a wire within the elongate body. The wire may extend proximally from the distal end portion of the elongate body through at least a portion of the elongate body. In a variation to the present aspect, the elongate body may also have a guidewire passageway, wherein the wire is a guidewire slideably engaged in the guidewire passageway. The guidewire passageway may have a proximal port along the proximal end portion of the elongate body and a distal port along the distal end portion of the elongate body. In another variation, the guidewire passageway may extend only through a portion of the elongate body.

The ablation elements employed in different modes of the tissue ablation system can comprise a microwave ablation element, a cryogenic ablation element, a thermal ablation element, a light-emitting ablation element (e.g., laser), an ultrasound transducer, or an electrical ablation element, such as an RF ablation element.

In a variation of the tissue ablation system of the present aspect, the ablation element may be adapted to form a linear lesion. In addition or in the alternative, the ablation element may be adapted to form a circumferential lesion, which may be formed at the location where a pulmonary vein extends from the left atrium.

Another aspect of the present invention includes a positioning system adapted to position and anchor one end of a medical device at a location where a pulmonary vein extends from the left atrium. The positioning system has a transeptal sheath which is inserted through the atrial septum that separates the right atrium from the left atrium. The positioning system also has an anchor device adapted to be positioned within the pulmonary vein. The anchor device has an elongate body with a proximal end portion and a distal end portion, and also has an expandable member along the distal end portion that is adjustable between a radially collapsed condition and a radially expanded condition that is adapted to engage the pulmonary vein.

The medical device preferably has a tracking mechanism adapted to slideably engage and track over the anchor device, such that advancing the medical device over the anchor device causes one end of the medical device to be positioned at the location where the pulmonary vein extends from the atrium. In one variation, the medical device is a mapping device with an electrode adapted to map a region of tissue at the location. In another variation, the medical device is an ablation device having an ablation element adapted to ablate a region of tissue at the location.

In modes where the medical device is an ablation device, the ablation element may be a microwave ablation element, a cryogenic ablation element, a thermal ablation element, a light-emitting ablation element, an ultrasound transducer, or an electrical ablation element, such as an RF ablation element.

In a variation of the tissue ablation system of the present aspect, the ablation element may be adapted to form a linear lesion. In addition or in the alternative, the ablation element may be adapted to form a circumferential lesion, which may be formed at the location where a pulmonary vein extends from the left atrium.

In one preferred mode of the positioning system, the expandable member is an inflatable balloon. In the present aspect, the elongate body may also comprise an inflation lumen, a pressurizable fluid source and a removable adapter on the proximal end portion of the elongate body. The adapter is adapted to couple the pressurizable fluid source to the inflation lumen. The balloon has an outer diameter of from about 0.114" to about 0.122" when inflated. The balloon may be made from any low density polymers or copolymers known in the art, such as polyethylene, polypropylene, polyolefins, PET, nylon, urethane, silicon, or Cflex.

In accordance with another variation of the positioning system, the anchor device of the tissue ablation system may have a shaped distal tip distal of the expandable member. Preferably, the anchor device is torquable and steerable, such that the anchor device may be directed into the pulmonary vein by manipulation of the proximal end portion. The elongate body of the anchor device comprises a polymeric tube.

The elongate body of the anchor device may be more flexible in the distal end portion than the proximal end portion. Also, the elongate body may have an intermediate region between the distal and proximal end portions, wherein the wall thickness of the proximal end portion is greater than the wall thickness of the intermediate region, such that the proximal end portion possess sufficient push force and kink resistance.

In one preferred mode of the positioning system, the anchor device also comprises a wire within the elongate body. The wire may extend proximally from the distal end portion of the elongate body through at least a portion of the elongate body. In a variation to the present aspect, the elongate body may also have a guidewire passageway, wherein the wire is a guidewire slideably engaged in the guidewire passageway. The guidewire passageway may have a proximal port along the proximal end portion of the elongate body and a distal port along the distal end portion of the elongate body. In another variation, the guidewire passageway may extend only through a portion of the elongate body.

The present invention is also related to a method of ablating a region of tissue at a location where the pulmonary vein extends from the left atrium. The method comprises the steps of: inserting into the atrium an anchor device adapted to be positioned within the pulmonary vein and having an elongate body with a proximal end portion and a distal end portion, and also having an expandable member along the distal end portion; positioning the anchor device within the pulmonary vein; anchoring the distal end portion of the anchor device within the pulmonary vein by adjusting the expandable member from the radially collapsed condition to the radially expanded condition; providing an ablation catheter adapted to slideably engage and track over the anchor device and also having an ablation element adapted to couple to an ablation actuator; advancing the ablation catheter into the atrium over the anchor device until the ablation element is positioned at the location; actuating the ablation actuator to energize the ablation element; and ablating the region of tissue with the ablation element.

In a variation of the method, prior to inserting the anchor device, a transeptal sheath is inserted through the atrial septum that separates the right atrium from the left atrium. In a further variation of the method, a guide member having a preshaped distal portion may be inserted through the transeptal sheath from the right atrium into the left atrium, prior to inserting the anchor device. In still a further variation of the method, the preshaped distal portion of the guide member may be positioned within the left atrium so that it points toward the pulmonary vein, and the anchor device is then inserted into the left atrium through the guide member. In one preferred variation of the method, the guide member is removed prior to advancing the ablation catheter over the anchor device.

BRIEF DESCRIPTION OF THE DRAWINGS

FIG. 1A is a cross-sectional view of the preferred fixed corewire balloon anchor wire in accordance with a preferred mode of the present invention, in which the corewire extends along the entire length of balloon anchor wire.

FIG. 1B is a cross-sectional view of a variation of the fixed corewire balloon anchor wire of the present invention, in which the corewire extends only partially through the balloon anchor wire.

FIGS. 2A-C are transverse cross-sectional views of the balloon anchor wire illustrated in FIG. 1B, taken along lines, A-A, B-B and C-C, respectively.

FIG. 3A is a cross-sectional view of an over-the-wire variation of the balloon anchor wire of the present invention, in which a balloon anchor catheter slideably engages a guidewire and a balloon is expanded; FIG. 3B is an enlarged view of the balloon in FIG. 3A.

FIG. 5 is a perspective view of a transeptal sheath in accordance with the present invention.

FIGS. 6A-D are perspective views of variations of a pre-shaped guide member in accordance with the present invention.

FIG. 8 is a perspective view of a variation of the ablation catheter of the present invention showing a proximal guidewire.

DETAILED DESCRIPTION OF THE PREFERRED EMBODIMENT

Balloon Anchor Wire

Figure 4:
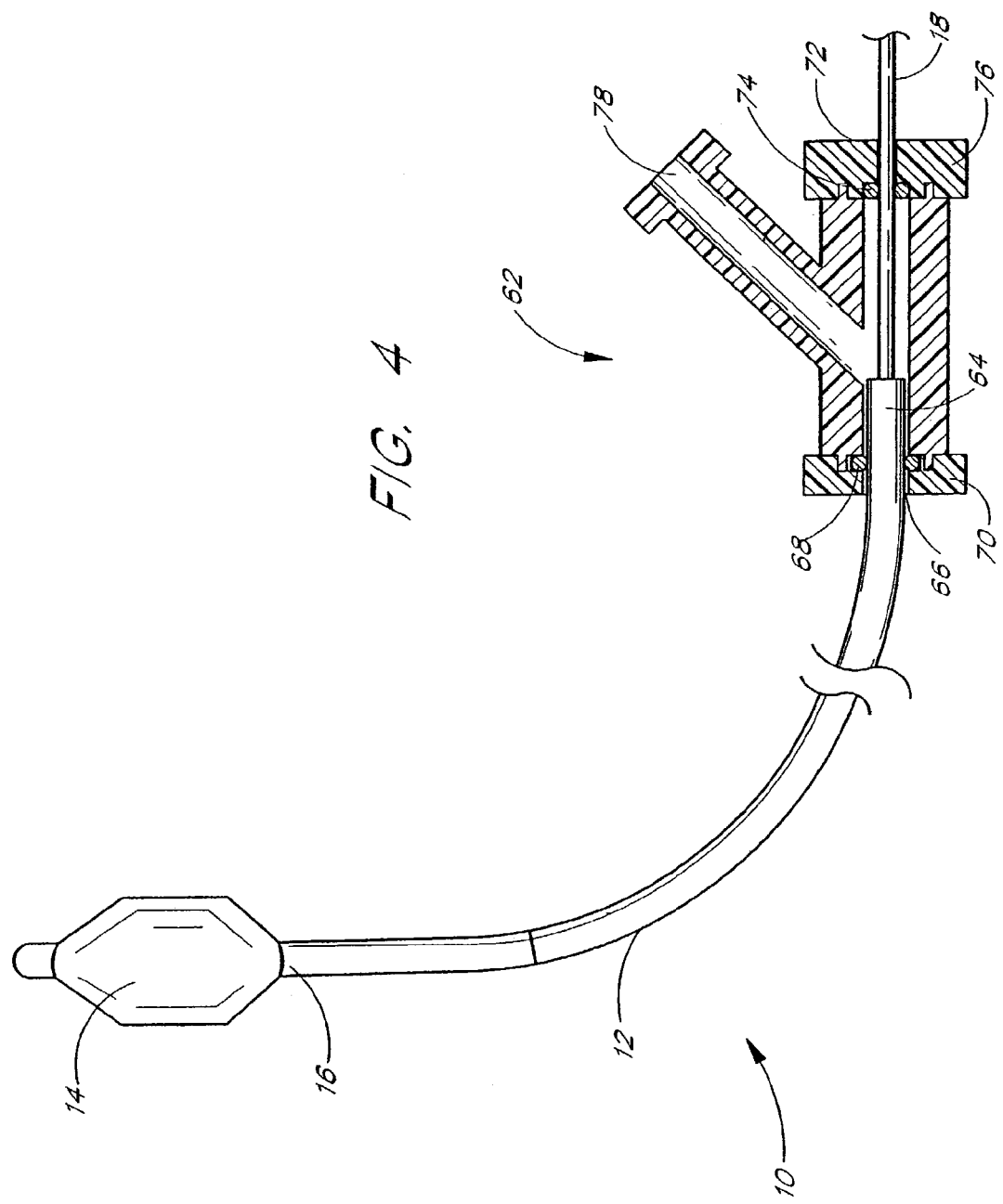
FIG. 4 is a perspective view of the fixed corewire variation of the balloon anchor wire showing the Y-adapter on the proximal end of the balloon anchor wire.

A cross-sectional view of the preferred "fixed corewire" balloon anchor wire of the present invention is shown in FIG. 1A. The balloon anchor wire 10 consists of a tubular member 12 with a balloon 14 attached to the distal region 16 of the tubular member. The tubular member is fitted over an integral corewire 18. The corewire 18 extends through the entire length of the tubular member, providing support (e.g., enhancing push force and kink resistance). The distal region 20 of the corewire 18 is tapered providing greater flexibility to the distal region 16 of the tubular member. The distal end 22 of the corewire 18 is bonded to the distal end 24 of the tubular member 12. The bond between the corewire and the tubular member is airtight, so that the balloon can be inflated. A wire coil 26 may be placed over the distal end 22 of the corewire to help provide support to the corewire and prevent kinking. Preferably, the wire coil 26 protrudes distally from the balloon as illustrated in FIGS. 1A & B to aid in atraumatic navigation of vessel branches.

Where the preferred continuous corewire design illustrated in FIG. 1A is employed, the tubular member 12 may have only two distinct regions corresponding in transverse cross-section to FIG. 2B and FIG. 2C. However, where the corewire 18 extends only partially through the tubular member, as shown in FIG. 1B, it may terminate anywhere proximal to the balloon 14. In this variation, the tubular member may comprise distinct proximal 28, intermediate 30, and distal 16 regions, in which the corewire terminates in the proximal region 28 of the tubular member 12. In such case, the proximal region 28 of the tubular member 12 is constructed of a heavier gage polymer (see cross-sectional view, FIG. 2A), capable of providing the necessary push force and kink resistance, which is provided by the corewire 18 in the continuous corewire design of FIG. 1A.

Transverse cross-sectional views of the tubular member of FIG. 1B are shown in FIGS. 2A-C for the proximal region 28, taken through lines A-A, the intermediate region 30, taken through lines B-B, and the distal region 16, taken through lines C-C. The corewire 18 is shown in the center of the distal 16 and intermediate 30 regions; note the diameter of the corewire 18 is smaller in the distal region 16 (FIG. 2C) than in the intermediate region 30 of the tubular member (FIG. 2B). No corewire is present throughout most of the proximal region 28 of the tubular member, as shown in FIG. 2A.

The wall 32 of the distal region 16 of the tubular member, which is supported by the integral corewire (FIG. 2C), is composed of a relatively thick layer (about 0.005" to about 0.015", preferably about 0.010" to 0.012) of low density polymer, such as polyethylene, from which the balloon is formed. In contrast, the wall 34 of the intermediate region of the tubular member, which is also supported by the integral corewire (FIG. 2B), is composed of a much thinner layer (about 0.001" to about 0.010", preferably about 0.004" to 0.005") of a higher density polymer, such as polyimide. The wall 36 of the proximal region (FIG. 2A) of the tubular member, which is not supported by an underlying corewire in the FIG. 1B variation of the balloon anchor wire, is composed of the same high density polymer as the intermediate region, but of a thickness (about 0.005" to about 0.015", preferably about 0.010" to 0.012") like that of the distal region. The thicker gage high-density polymer construction is necessary in the proximal region absent a continuous corewire, in order to provide sufficient pushing force. In the preferred continuous corewire design, the walls of the tubular member may be constructed out of the same polymeric material of approximately the same gage along the entire length of the balloon anchor wire. Consequently, there may be no distinct regions, having instead only relative proximal and distal regions.

The inside diameter of the tubular member 12 is sufficiently large in relation to the outer diameter of the corewire 18 along the entire length of the tubular member that an inflation lumen 38 is created between the inner wall 40 of the tubular member and the outer surface 42 of the corewire in the intermediate 30 and distal 16 regions of the tubular member (FIGS. 2B & C). In the proximal region 28, where no corewire is present (FIG. 2A), the inflation lumen 38 comprises the entire lumen of the tubular member. In another variation of the balloon anchor wire, a separate inflation lumen may reside within the balloon anchor wire or along the outside of the balloon anchor wire. An inflation medium (i.e., air, saline or contrast) can be passed through the inflation lumen 38 to inflate the balloon 14.

With reference to FIG. 3, an over-the-wire variation of the balloon anchor wire of the present invention is shown. The balloon anchor wire 10 still consists of a tubular member 12 and a distally located balloon 14. However, a guidewire 44 is slideably engaged within a guidewire passageway 46 that runs longitudinally through the entire length of the balloon anchor wire 10. An inflation lumen 38 is also present between the inner wall 40 of the tubular member 12 and the outer wall 48 of the guidewire passageway 46 to permit balloon inflation and deflation as described above.

A perspective view of a preferred fixed corewire balloon anchor wire of the present invention is shown in FIG. 4 with a removable Y-adapter 62. The shaft 12 of the balloon anchor wire 10 has a proximal end 64 which is inserted into the distal end 66 of the Y-adapter 62 and is engaged therein by a distal O-ring 68. The distal O-ring 68 can be adjustably tightened and loosened on the proximal end 64 of the shaft by turning the distal knob 70 which is threaded onto the distal end 66 of the Y-adapter. The corewire 18 exits the proximal end 72 of the Y-adapter 62. A proximal O-ring 74 engages the corewire. The proximal O-ring 74 can be adjustably tightened and loosened on the corewire by turning the proximal knob 76 which is threaded onto the proximal end 72 of the Y-adapter 62. A fluid port 78 is in fluid communication with the inflation lumen created between the outer surface of the corewire and the inner wall of the tubular member, thereby allowing inflation and deflation by conventional means of the balloon 14 along the distal region 16 of the balloon anchor wire when the proximal 74 and distal 68 O-rings are tightened.

Positioning and Anchoring System

In addition to the balloon anchor wire disclosed above, other guide components comprise a system disclosed for use in positioning and anchoring a linear ablation element along the wall of the left atrium. Included among the additional system components are a transseptal sheath and a preshaped guide member. A perspective view of the transseptal sheath in accordance with the present invention is illustrated in FIG. 5. The sheath 50 has proximal 52 and distal 54 regions. The transseptal sheath 50 is inserted through the atrial septum, preferably at the fossa ovalis, with the distal region 54 residing in the left atrium in order to facilitate atraumatic entry and withdrawal of the guide member, balloon anchor wire and ablation catheter into the left atrium during the ablation procedure as needed. The transseptal sheath 50 can be constructed from any conventional polymeric materials and may have a diameter of approximately 8-15 F, preferably about 12 F.

With reference to FIGS. 6A-D, perspective views of various guide members are shown. Each guide member 56 has proximal 58 and distal 60 portions and can be constructed from conventional polymeric materials. The distal portion 60 of the guide member is preshaped so that the distal end 62 can be positioned to point toward a predetermine pulmonary vein by adjustably advancing and retracting the guide member 56 through the transseptal sheath 50 (shown in FIG. 5) and by torquing the proximal end 58 of the guide member 56. The guide member in accordance with the present invention may have any shape consistent with the purpose of the guide member to direct the balloon anchor wire toward a predetermined pulmonary vein. The diameter of the guide member 56 is approximately 5-10 F, preferably about 7 F, thereby permitting the guide member 56 to enter the left atrium by sliding within the transseptal sheath 50 (shown in FIG. 5).

Figure 7A:
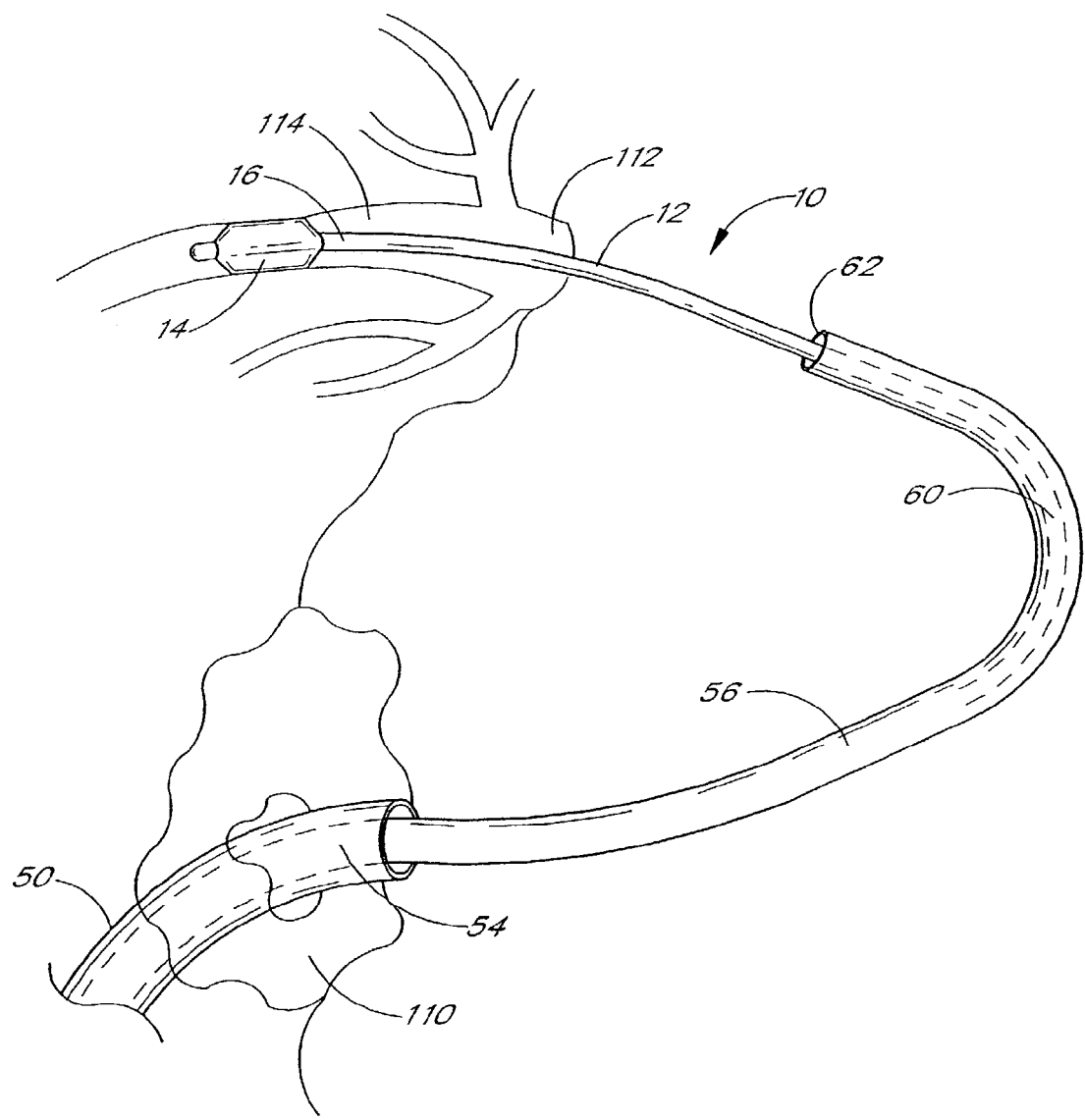
FIG. 7A is a schematic view of the guide system of the present invention showing the relationship of the transeptal sheath, the pre-shaped guide member and the balloon anchor wire in situ.

A variation of the positioning and anchoring system of the present invention is shown in situ in FIG. 7A. The transseptal sheath 50 traverses the atrial septum 110 that separates the right and left atria. The distal end 54 of the transseptal sheath opens into the left atrium. Emerging from and slideably engaged within the transseptal sheath 50 is the preshaped guide member 56. The distal portion 60 is shaped such that the distal end 62 is pointing toward the predetermined pulmonary vein. Emerging from and slideably engaged within the guide member 56 is the balloon anchor wire 10. The balloon anchor wire 10 is shown passing through the pulmonary vein ostium 112, such that the distal region 16 of the tubular member 12 and the anchoring balloon 14 are located well within the pulmonary vein 114.

Figure 7B:
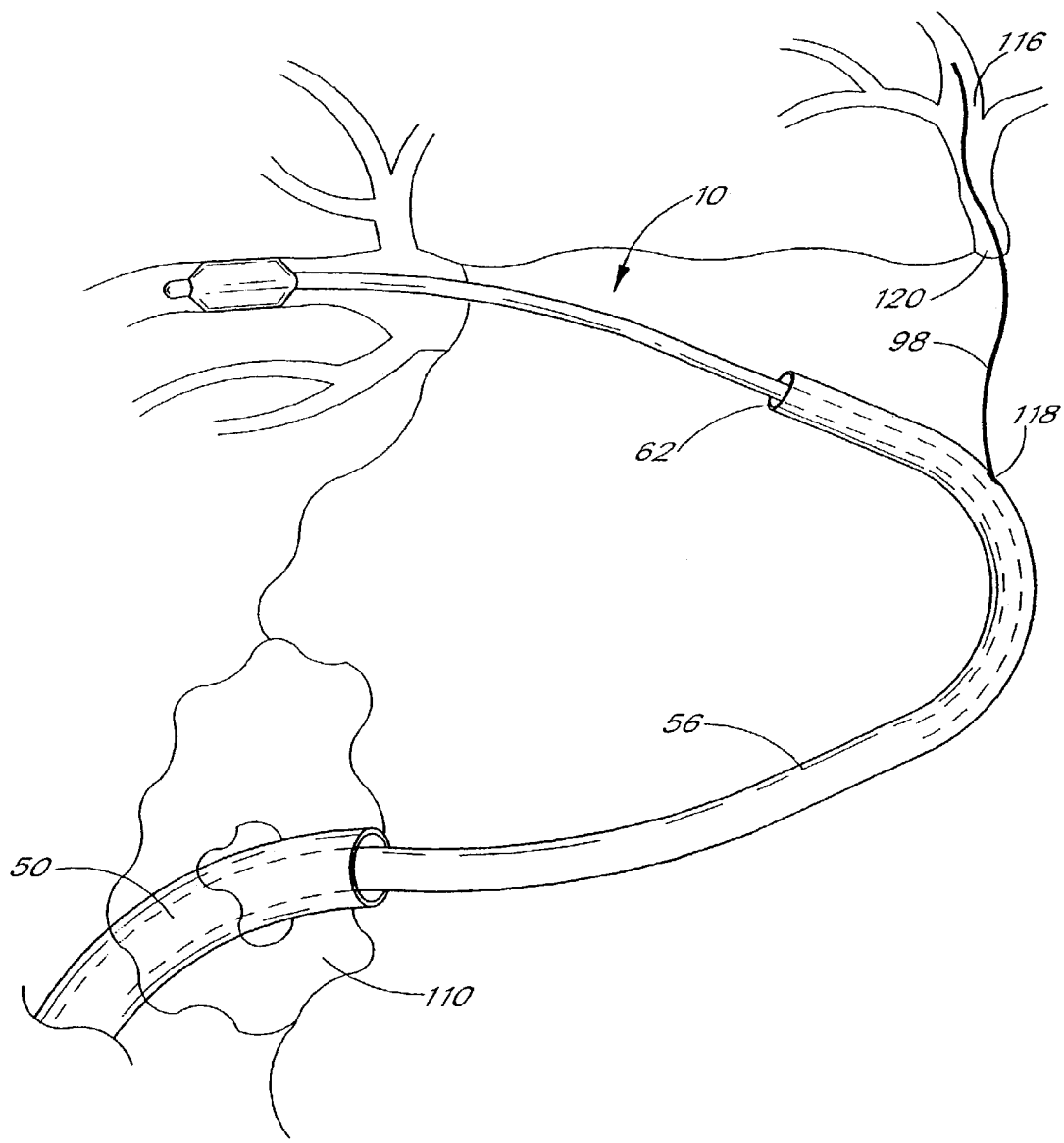
FIG. 7B is a schematic view of the proximal guidewire variation of the guide system of the present invention, showing the relationship of the transeptal sheath, the pre-shaped guide member, the balloon anchor wire and the proximal guidewire in situ.

A preferred variation of the positioning and anchoring system of the present invention is shown in situ in FIG. 7B. Like FIG. 7A, the transseptal sheath 50 penetrates the atrial septum 110. The preshaped guide member 56 is slideably engaged in the transseptal sheath 50 and the balloon anchor wire 10 is slideably engaged in the guide member 56. In this variation, however, the guide member 56 is further adapted to direct a guidewire 98 into a second pulmonary vein 116. The guide member 56 has a guidewire lumen which terminates in a guidewire port 118 located proximal to the distal end 62 of the guide member and facing the ostium 120 of the second pulmonary vein 116, whereby advancing the guidewire 98 results in cannulation of the second pulmonary vein 116 by the guidewire 98.

Linear Ablation Catheter

An ablation catheter 80 in accordance with the present invention is illustrated in FIG. 8. The ablation catheter 80 consists of a tubular member 82 with a distal portion 84 having a tracking means 86 which is adapted to slideably engage and track along the balloon anchor wire of the present invention, such that the distal portion 84 of the ablation catheter 80 can be directed toward a first pulmonary vein within which the balloon anchor wire has been anchored. Proximal to the tracking means 86 is a linear ablation element 88. The ablation element has a distal end 90, located proximal to and adjacent the tracking means 86, and a proximal end 92, wherein an ablation length 94 is defined by the distal 90 and proximal 92 ends of the ablation element 88.

In the preferred variation of the ablation catheter illustrated in FIG. 8, a guidewire port 96 is located along the tubular member 82, proximal to and adjacent the proximal end 92 of the ablation element 88. The guidewire 98 may extend from a second pulmonary vein, within which it was fed using the guide member prior to introducing the ablation catheter into the left atrium, such that the proximal end 92 of the ablation element 88 can be directed toward the ostium of the second pulmonary vein by tracking along the guidewire 98. Note, however, that in another variation to the illustrated ablation catheter, no guidewire may be included, wherein there is provided no specific guiding means for targeting a second pulmonary vein ostium.

The ablation catheter 80 also has a proximal portion 100 that is located outside of the patient's body during the ablation procedure. The proximal portion 100 has a fluid port 102, through which an electroconductive and/or cooling solution, like saline, can be introduced for the purpose of facilitating complete transmural tissue ablation with minimal burning and coagulation of the surrounding blood. The proximal portion of the ablation catheter may also have a stylet port 104, through which a stylet may be introduced in order to push the ablation catheter 80 against the atrial wall or better anchor the proximal end 92 of the ablation element 88 within the second pulmonary vein ostium. A third possible port in the proximal portion of the ablation catheter is the proximal guidewire port 106, through which the guidewire 98 may proximally exit the catheter. In embodiments of the ablation catheter containing no guidewire for locating the second pulmonary vein, there need be no guidewire port in the proximal portion of the ablation catheter. Finally, the proximal end of the ablation catheter has an electrical connector 108, through which lead wires from ablation electrodes which comprise the ablation element 88 may exit the ablation catheter and be coupled to an ablation actuator, such that actuating the ablation actuator will energize the ablation element, thereby ablating the length of tissue and forming a conduction block.

It is contemplated that the subject matter disclosed herein may be combined with various embodiments which have formed the subject matter of other contemporaneous or previous patent filings, including without limitation the embodiments shown and described in the following filed provisional and non-provisional U.S. Patent Applications and issued U.S. Patents:

(1) U.S. patent application Ser. No. 08/853,861 filed May 9, 1997 for "Tissue Ablation Device And Method Of Use", now U.S. Pat. No. 5,971,983;

(2) U.S. patent application Ser. No. 08/889,798 filed Jul. 8, 1997 for "Circumferential Ablation Device Assembly", now U.S. Pat. No. 6,024,740;

(3) U.S. patent application Ser. No. 08/889,835 filed Jul. 8, 1997 for "Device And Method For Forming A Circumferential Conduction Block In A Pulmonary Vein", now U.S. Pat. No. 6,012,457;

(4) U.S. patent application Ser. No. 09/073,907 filed May 6, 1998 for "Tissue Ablation Device With Fluid Irrigated Electrode";

(5) U.S. patent application Ser. No. 09/199,736 filed Nov. 25, 1998 for "Circumferential Ablation Device Assembly";

(6) U.S. patent application Ser. No. 09/240,068 filed Jan. 29, 1999 for "Device And Method For Forming A Circumferential Conduction Block In A Pulmonary Vein";

(7) U.S. patent application Ser. No. 09/260,316 filed Mar. 1, 1999 for "Tissue Ablation System And Method For Forming Long Linear Lesion";

(8) Provisional U.S. Application No. 60/122,571, Filed on Mar. 2, 1999 for "Feedback Apparatus And Method For Ablation At Pulmonary Vein Ostium";

(9) Provisional U.S. Application No. 60/125,509, filed Mar. 19, 1999 for "Circumferential Ablation Device Assembly And Methods Of Use And Manufacture Providing An Ablative Circumferential Band Along An Expandable Member";

(10) Provisional U.S. Application No. 60/125,928, filed Mar. 23, 1999 for "Circumferential Ablation Device Assembly And Methods Of Use And Manufacture Providing An Ablative Circumferential Band Along An Expandable Member";

(11) Provisional U.S. Application No. 60/133,807, filed May 11, 1999 for "Catheter Positioning System";

(12) Provisional U.S. Application No. 60/133,680, filed May 11, 1999 for "Apparatus And Method Incorporating An Ultrasound Transducer";

(13) Provisional U.S. Application No. 60/133,677, filed May 11, 1999 for "Tissue Ablation Device Assembly And Method For Electrically Isolating A Pulmonary Vein Ostium From A Posterior Left Atrial Wall";

the disclosures of these references are herein incorporated in their entirety by reference.

Exemplary variations of the tissue ablation catheter include ablation assemblies having an irrigated ablation member that is attached to a delivery member in order to access and position the ablation member at the site of the target tissue. The delivery member takes the form of an over-the-wire catheter, wherein the "wire" is the balloon anchor wire. The delivery member comprises an elongated body with proximal and distal end portions. As used herein, the terms "distal" and "proximal" are used in reference to a source of fluid located outside the body of the patient. The elongated body preferably includes a balloon anchor wire lumen, an electrical lead lumen and a fluid lumen, as described in greater detail below.

Each lumen extends between a proximal port and a respective distal end. The distal ends of the lumens extend through the ablation member, as described in greater detail below. Although the balloon anchor wire, fluid and electrical lead lumens may assume a side-by-side relationship, the elongated body can also be constructed with one or more of these lumens arranged in a coaxial relationship, or in any of a wide variety of configurations that will be readily apparent to one of ordinary skill in the art.

The elongated body of the delivery member and the distally positioned ablation member desirably are adapted to be introduced into the left atrium, preferably through the transseptal sheath. Therefore, the distal end portion of the elongated body and the ablation member are sufficiently flexible and adapted to track over and along a balloon anchor wire positioned within the right or left atrium, and more preferably seated within one of the pulmonary veins that communicates with the left atrium. In an exemplary construction, the proximal end portion of the elongated body is constructed to be at least 30% stiffer than the distal end portion. According to this relationship, the proximal end portion may be suitably adapted to provide push transmission to the distal end portion while the distal end portion and the ablation member are suitably adapted to track through bending anatomy during in vivo delivery of the ablation member into the desired ablation region.

A more detailed construction for the components of the elongated body, which is believed to be suitable for use in transseptal left atrial ablation procedures, is as follows. The elongated body itself may have an outer diameter provided within the range of from about 3 French to about 11 French, and more preferably from about 7 French to about 9 French. The balloon anchor wire lumen preferably is adapted to slideably receive balloon anchor wires ranging from about 0.010 to about 0.038" in diameter, and preferably is adapted for use with balloon anchor wires ranging from about 0.018" to about 0.035" in diameter. Where a 0.035" diameter balloon anchor wire is to be used, the balloon anchor wire lumen desirably has an inner diameter of 0.040" to about 0.042". In addition, the fluid lumen desirably has an inner diameter of about 0.019" in order to permit ample irrigation of the ablation member.

The elongated body comprises an outer tubular member that houses at least three inner tubings: an electrical lead tubing, a fluid tubing, and a balloon anchor wire tubing. Each of the tubings extends at least from the proximal end portion of the elongated body to the distal end portion, and at least partially through the ablation member, as described below. The tubings are arranged in a side-by-side arrangement; however, as noted above, one or more of the tubings can be arranged in a coaxial arrangement. In one mode, the inner tubings are polyimide tubes. Such tubing is available commercially from Phelps Dodge, of Trenton, Ga. The electrical lead and fluid tubings desirably have a 0.019" inner diameter and a 0.023" outer diameter, while the balloon anchor wire tubing is slightly larger, as indicated above. The outer tubular member comprises a thermoplastic, such as, for example, a urethane or vinyl material. A suitable material for this application is Pebax of a grade between 3533 to 7233, and of an outer diameter of about 0.064".

Notwithstanding the specific delivery device constructions just described, other delivery mechanisms for delivering the ablation member to a desired ablation region are also contemplated. For example, while an "over-the-wire" catheter construction was described, other balloon anchor wire tracking designs may also be suitable substitutes, such as for example catheter devices known as "rapid exchange" or "monorail" variations wherein the balloon anchor wire is only housed within a lumen of the catheter in the distal regions of the catheter. In another example, a deflectable tip design may also be a suitable substitute. The latter variation can also include a pullwire which is adapted to deflect the catheter tip by applying tension along varied stiffness transitions along the catheter's length. Further more detailed examples of deflectable tip members are disclosed in the following references: U.S. Pat. No. 5,549,661 to Kordis et al.; PCT Publication WO 94/21165 to Kordis et al.; and U.S. Pat. No. 5,592,609 to Swanson et al.; PCT Publication WO 96/26675 to Klein et al. The disclosures of these references are incorporated herein in their entirety by reference thereto.

The proximal end portion of the elongated body terminates in a coupler. In general, any of several known designs for the coupler is suitable for use with the present tissue ablation device assembly, as would be apparent to one of ordinary skill. For example, a proximal coupler may engage the proximal end portion of the elongated body of the delivery member. The coupler includes an electrical connector that electrically couples one or more conductor leads, which stem from the ablation member and extend through the electrical lead tube, with an ablation actuator. The coupler also desirably includes another electrical connector that electrically couples one or more temperature sensor signal wires to a controller of the ablation actuator.

As known in the art, the ablation actuator is connected to both of the electrical connectors and to a ground patch. A circuit thereby is created which includes the ablation actuator, the ablation member, the patient's body, and the ground patch that provides either earth ground or floating ground to the current source. In the circuit, an electrical current, such as a radiofrequency, ("RF") signal may be sent through the patient between the ablation member and the ground patch, as well known in the art.

The coupler may also include a fluid coupler. The fluid coupler is adapted to be coupled to a source of pressurized fluid (e.g. saline solution) so as to irrigate the ablation member, as described below. The fluid coupler communicates with the fluid tube to supply the ablation member with a source of pressurized fluid.

The ablation member has a generally tubular shape and includes an ablation element. The phrase "ablation element" as used herein means an element that is adapted to substantially ablate tissue in a body space wall upon activation by an actuator. The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue. The term "element" within the context of "ablation element" is herein intended to mean a discrete element, such as an electrode, or a plurality of discrete elements, such as a plurality of spaced electrodes, which are positioned so as to collectively ablate a region of tissue. Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type that is adapted to emit energy sufficient to ablate tissue when coupled to and energized by an energy source.

Suitable "energy emitting" ablation elements for use in the present invention may therefore include, for example, but without limitation: an electrode element adapted to couple to a direct current ("DC") or alternating current ("AC") source, or a radiofrequency ("RF") current source; an antenna element which is energized by a microwave energy source; a heating element, such as a metallic element or other thermal conductor which is energized to emit heat such as by convection or conductive heat transfer, by resistive heating due to current flow, a light-emitting element such as a laser, or an ultrasonic element such as an ultrasound crystal element which is adapted to emit ultrasonic sound waves sufficient to ablate tissue when coupled to a suitable excitation source. It also is understood that those skilled in the art can readily adapt other known ablation devices for use with the present ablation member.

In a preferred mode, the ablation element includes a plurality of electrodes that are arranged over a length of the ablation member next to one another (i.e., are arranged in series in the spatial sense). The length from the proximal-most electrode to the distal-most electrode defines an ablation length, which is less than a working length of the ablation element, as described below.

At least one conductor lead connects to the electrodes. The number of conductor leads is desirably equal to the number of electrodes to allow for independent control of each electrode under some modes of operation. Each conductor is a 36 AWG copper wire insulated with a 0.0005" thick polyimide coating. Each conductor exits the electrical lead tube at a point near a corresponding electrode. A distal end of each wire is exposed and is electrically coupled to the corresponding electrode in the manner described below. The proximal end of each conductor lead is connected to the electrical connector on the proximal end of the tissue ablation device assembly.

An irrigation mechanism may irrigate the ablation element. The irrigation mechanism is adapted to provide a generally even flow of fluid about each of the electrodes along the length of the ablation member. The irrigation mechanism can be configured to discharge fluid either in a radial direction (i.e., generally normal to the longitudinal axis) or in the longitudinal direction, or in both directions, as illustrated by the below described variations of the ablation member.

The irrigation mechanism desirably includes an inner space defined within a porous, fluid-permeable membrane. The membrane desirably has a generally tubular shape and extends along at least a portion of the ablation member's length; however, the membrane need not be tubular or cover the entire ablation member. The membrane though preferably is arranged to face the target tissue once the ablation element is delivered to and positioned within the particular body space. The membrane has a length, as measured in the longitudinal direction, which is greater than a distance between the proximal-most and distal-most electrodes of the series. The membrane's length is defined between its proximal and distal ends.

The porous membrane includes an inner surface and an outer surface that define the boundaries of a porous wall. The wall is formed of a porous, biocompatible, generally non-compressible material. As used herein, the term "non-compressible" means that the material generally does not exhibit appreciable or sufficient compressibility between its inner and outer surfaces to conform to surface irregularities of the tissue against which the ablation member is placed. The material, however, is sufficiently flexible in the longitudinal direction (i.e., deflectable) so as to track over and along a balloon anchor wire positioned within the left atrium, and more preferably seated within one of the pulmonary veins that communicates with the left atrium. In other words, the material of the tubular porous membrane allows it to bend through a winding access path during in vivo delivery of the ablation member into the desired ablation region.

The porous nature of the membrane's material also permits a fluid to pass through the membrane upon the application of a sufficient pressure differential across the membrane. Fluid thus does not freely flow through the membrane. The degree of porosity of the membrane over its length also desirably is uniform. This uniformity coupled with the flow restrictiveness of the material results in the fluid emanating from the member in a generally even flow over the entire membrane outer surface.

Exemplary porous materials suitable for this application include expanded polytetrafluoroethylene (PTFE), porous polyethylene, porous silicon, porous urethane, and tight weaves of Dacron. Such porous materials are formed using conventional techniques, such as, for example by blowing the material or by drilling micro holes within the material. The porosity of the material desirably ranges between about 5 and 50 microns. An acceptable form of the porous PTFE material is available commercially from International Polymer Engineering, of Tempe, Ariz., as Product Code 014-03. It has been found that fluid will pass through this material upon applying a relatively low pressure within the material (e.g., 5 psi). In an exemplary form, the membrane is formed of a tubular extrusion of this material which has an inner diameter of about 0.058" and an outer diameter of about 0.068" for applications involving ablation of myocardial tissue via an arterial or venous access path. For other applications, such as, for example, ablation within small coronary vessels, a significantly smaller diameter size can be used.

The porous membrane is attached to the distal end portion of the delivery member, as noted above. The proximal end of the porous membrane is interposed between the distal end portion of the elongated body and a sealing member. That is, the tubular proximal end of the porous member is placed over the distal end of the elongated body outer tube. The sealing member then is slipped over this assembly and arranged to lie generally above the overlapping sections of the tube and the membrane.

The sealing member desirably is formed of a material similar to or compatible with the material of the elongated body in order to heat-melt bond these two components together. In an exemplary form, the sealing member comprises Pebax of a similar grade used for the outer tube of the elongated body. This bonding process occurs with the proximal end of the porous member positioned between the outer tube distal end and the sealing member.

The porous membrane also desirably includes one or more openings that extend through the wall of the porous membrane. These openings are formed (e.g., punched) on the proximal end of the membrane prior to the bonding procedure, and can take the form of holes or longitudinal slots that extend into the membrane from the proximal end; of course, other shapes of openings can also be used. The similar plastic materials of the seal member and the elongated body outer tube fuse together within these openings and bond under and over the porous material of the membrane during the bonding process. This coupling securely attaches the porous membrane to the distal end portion of the elongated body.

The porous membrane of course can be joined to the distal end portion of the elongated body in any of a variety of other ways well known to those skilled in the art. For instance, the proximal end of the porous membrane can be bonded to the outer tube distal end using a biocompatible adhesive, such as, for example, cyanoacrylate available commercially from Loctite7 of Rockyhill, Conn., as Part No. 498.

An end cap closes the distal end of the porous membrane. The end cap desirably has a tapering shape that decreases in diameter distally. On its distal end, the end cap includes a port that aligns with the distal end of the balloon anchor wire tube when assembled. The end cap also includes an inner opening defined in part by a collar section. The inner diameter of the collar section is sized to receive the distal ends of the tubings and the outer diameter of the collar is sized to slip within the distal end of the porous membrane.

The end cap desirably is formed of a biocompatible plastic material, such as, for example, urethane or vinyl. In a preferred mode, the end cap is formed of same material that comprises the outer tube of the elongated body, such as, Pebax of a grade between 3533 to 7233, and of an outer diameter of about 0.064".

The end cap and the distal end of the porous membrane desirably are secured together in a similar fashion to that described above. As such, a heat melt bond is formed between a second sealing member and the distal end cap, with the distal end of the porous member being interposed between these elements. The similar plastic materials of the sealing member and the end cap fuse together within openings in the porous membrane at its distal end, as well as over and under the porous membrane. Other bondings can also be used as described above.

The balloon anchor wire tube, the fluid tube, and the lead wire tube each extend within the porous membrane in a longitudinal direction to the distal end cap.

The electrical lead tube functions as a wiring harness and carries one or more conductors or wires that are attached to the electrodes. The tube extends beyond the distal end portion of the elongated body, through the porous membrane and terminates at a point within the distal end cap. A plug seals the distal end of the electrical lead tube. In an exemplary form, the plug is formed by filling the distal end of the tube with Cyanoaerylat7.

The balloon anchor wire tube extends entirely through the ablation member and the distal end cap, and communicates with a distal port formed in the end cap. The distal port is sized to receive the balloon anchor wire over which the elongated body and the ablation member track. The port, thus, allows the balloon anchor wire to pass through the end cap. In a variation, the balloon anchor wire tube can replace the end cap with the porous membrane attaching directly to the tube. In such an embodiment, the other tube will stop short of the distal end of the ablation member.

The fluid tube defines a pressurizable fluid passageway. The fluid tube extends beyond the distal end portion of the elongated body, through the porous membrane and terminates at a point within the distal end cap next to a distal end of the electrical lead tube. Another plug seals the distal end of the fluid tube. In an exemplary form, the plug is formed by filling the distal end of the tube with Loctite7. The tube, however, can terminate proximal of the electrodes but distal of the proximal membrane seal.

The fluid tube includes at least one opening which opens into the inner space defined within the porous membrane. In this manner, the pressurizable fluid passageway or lumen provided by the irrigation tube communicates with the inner space of the ablation member. A single slot is formed near a proximal end of the inner space; however, several slots or holes can be formed along the section of the irrigation tube that extends through the inner space.

A proximal end of the inner space desirably is sealed to prevent a flow of fluid proximally. In the present variation, the distal end of the inner space is also sealed. This allows the pressure within the inner space to be increased to promote fluid weeping through the wall of the porous membrane, as described in greater detail below. The above-described sealing technique provides an adequate seal. In the alternative, a seal can be formed at each location by heat shrinking polyethylene teraphthalate (PET) over the tubes. The proximal seal has an outer diameter of a sufficient size to plug the passage through the elongated body at the distal end of the body and the distal seal has an outer diameter of sufficient size to plug the opening defined by the collar in the distal end cap.

Each electrode in the ablation element comprises a wire coil formed in a helical pattern. The electrodes desirably have identical configurations, and thus, the following description of one is understood to apply equally to all, unless indicated otherwise.

Each coil electrode has a sufficiently large inner diameter to receive tubings, while its outer diameter is sized to fit within the tubular porous membrane. In an exemplary form, each ablation element comprises a 0.005" diameter wire made of a biocompatible material (e.g., stainless steel, platinum, gold-plated nitinol, etc.). The wire is unshielded and is wound in a helical fashion with about a 0.048" inner diameter. The coils are spaced along the lengths of the tubings that extend longitudinally through the porous membrane. In an exemplary mode, each coil has a length, as measured in the longitudinal direction, of about 0.28" and is spaced from an adjacent coil by a distance of about 0.08".

The corresponding conductor wire passes through a hole in the electrical lead tubing and is soldered to the coil with a 95 Ag/5 Sn. The conductor wire can also be electrically connected to the electrodes by other means, such as, for example, by resistant, ultrasonic or laser welding. In addition, the coil and the conductor can be unitary by winding the distal end of the conductor in a helical pattern. Known electrical connectors can also be used to electrically couple the conductor to the corresponding electrode.

The electrodes of the ablation member desirably have sufficient flexibility to bend to track through a venous or arterial access path to an ablation target site. The electrodes can have a variety of configurations as long as they afford similar flexibility. For instance, the electrode can have a tubular or cylindrical shape formed by a plurality of braided wires. The end bands link the ends of the wires together to prevent the braided structure from unraveling. The end bands can also electrically couple the wires together. The bands though are sufficiently narrow so as not to meaningfully degrade the flexibility of the ablation element. Any braided pattern can work, but a "diamond" pattern mesh is preferred. The wires of the braid can either have rectangular ("flat") or rounded cross sections. The wire material can be any of a wide variety of known biocompatible materials (such as those identified above in connection with the coil electrodes). In one mode, the braided electrode can be "wounded" before inserting into the tubular porous membrane. Once inserted, the electrode can be uncoiled to press against the inner surface of the tube. In this manner, the membrane can support the electrode.

An electrode can be constructed where the electrode is formed from a flat wire mesh that has been rolled into an arcuate structure. The structure may have a semi-cylindrical shape; however, the structure can extend through either more or less of an arc. Alternatively, the electrode may have a "fishbone" pattern, wherein the electrode includes a plurality of arcuate segments that extend from an elongated section which generally lie parallel to a longitudinal axis of the ablation member when assembled. The ends of each arcuate segment can be squared or rounded.

An electrode may also be formed in an "arches" pattern. A plurality of arch segments lie in series with two side rails interconnecting the corresponding ends of the arch segments. The arch segments are spaced apart from one another along the length of the electrode. Such embodiments can be formed by etching or laser cutting a tube of electrode material.

Common to all of the electrodes is the ability to flex. The flexibility of these electrodes allows them to bend through tight turns in the venous or arterial access path without collapsing. The electrodes also have low profiles so as to minimize the outer diameter of the ablation member. Fluid can also pass radially through the electrodes. Other types of electrode designs that exhibit these features can also be used. For example, the electrode can be formed in a manner resembling a conventional stent by etching or laser cutting a tube. The electrode also need not extend entirely about the longitudinal axis of the ablation member; the electrode can be generally flat and positioned on only one side of the catheter. A serpentine shape would provide such a flat electrode with the desired flexibility. However, in order for the ablation member to be less orientation sensitive, each electrode desirably extends through at least 180 degrees about the longitudinal axis of the ablation member. Accordingly, the foregoing electrode designs are merely exemplary of the types of electrodes that can be used with the present ablation member.

Although the following variations of the irrigation ablation member are described as including a coiled electrode, it is understood that any of foregoing designs, as well as variations thereof, can be used as well with these devices.

The tissue ablation device assembly also desirably includes feedback control. For instance, the ablation member can include one or more thermal sensors (e.g., thermocouples, thermisturs, etc.) that are provided to either the outer side or the inside of the porous membrane. Monitoring temperature at this location provides indicia for the progression of the lesion. The number of thermocouples desirably equals the number of electrodes so as to enhance the independent control of each electrode. If the temperature sensors are located inside the porous membrane, the feedback control may also need to account for any temperature gradient that occurs across the membrane.

The sensors placed on the exterior of the porous member may also be used to record electrogram signals by reconnecting the signal leads to different input port of the signal-processing unit. Such signals can be useful in mapping the target tissue both before and after ablation.

In the one embodiment, the temperature sensors each comprise an annular thermocouple that is positioned about the outer side of the porous membrane. In this location, the thermocouple lies on the outside of the membrane where it can directly contact the tissue-electrode interface. The thermocouple is isolated from direct metal-to-metal electrical contact with the electrodes because the thermocouples are separated by the porous membrane. Thus, separate insulation is not necessary.

The thermocouples desirably are blended into the outer surface of the ablation member in order to present a smooth profile. Transition regions formed by either adhesive or melted polymer tubing, "smooth out" the surface of the ablation member as the surface steps up from the porous member outer surface to the thermocouple surface.

Signal wires extend proximally from the thermocouples to the electrical connector on the proximal end of the tissue ablation device assembly. In the illustrated mode, the wires are shielded and extend into the porous membrane and then into the electrical lead tube. These wires can be routed proximally in other manners. For instance, the wires can form a braided structure on the exterior of the ablation member and then be pulled together and routed proximally along the side of the elongated body. The wires can also be routed proximally inside one or more tubes that extend parallel to and are attached to the elongated body. The wires can also be sewn into the wall of the outer tubing of the elongated body. These represent a few variations on various ways of routing the thermocouple wires to the proximal end of the tissue ablation device assembly.

In use, the electrical and fluid connectors of the proximal coupler are connected to the ablation actuator and the pressurized fluid source, respectively. A conventional grounding patch or other grounding device is placed against the patient.

The ablation member can be constructed in other forms while obtaining the above-noted advantages. For instance, the ablation member can include a different shaft construction from that described above. A balloon anchor wire tube may extend longitudinally through the ablation member and communicate with the distal port. The balloon anchor wire tube is positioned within a structure of braided wires. Each of the wires is insulated, and the wires desirably are woven in a diamond-like pattern.

The braided structure desirably includes at least an inner or an outer coating of a plastic material so as to define a pressurizable fluid passageway. An inner layer and an outer layer of polymer are laminated over the braid structure to define a generally fluid-impermeable structure. The polymer layers stop at the distal end of the elongated body though. The braided structure continues distally to form a support structure for the ablation member. Fluid can pass through the uncoated braided structure.

The braided structure supports the electrodes. The electrodes are spaced along the length of the braided structure to define the linear ablation element. One of the wires from the braid is connected to a corresponding electrode. Any of the above-described connectors can be used to electrically couple an unshielded end of the conductor wire to the corresponding electrode.

Although not illustrated, a spacer may be placed between adjacent electrode pairs to prevent fluid from flowing through a corresponding section of the braided structure not covered by an electrode. The spacers can be formed of a polymer or an epoxy attached directly to the braided structure. The absence of a spacer, however, provides a fluid flow between the electrodes that may be beneficial in some applications.

The porous membrane covers the electrodes supported by the braided structure. A proximal end of the porous membrane is secured to the distal end of the elongated body, as defined by the distal end of the laminate structure. The proximal end of the porous membrane can be attached in any of the above-described manners.

Similarly, the distal end of the porous membrane is attached to an end cap. The end cap includes an elongated collar that receives a distal end of the braided structure. The distal end of the porous membrane extends over the collar and is secured thereto in any of the above-described manners.

The ablation member can also include one or more thermocouples. The thermocouples are attached to the porous membrane in the manner described above. The thermocouple wires extend through the membrane and through the braided structure, and are routed proximally through the inner lumen of the braided structure that defines the pressurizable fluid passageway. The proximal ends of the thermal couple wires are connected to an electrical connector of a proximal coupler.

Another variation of the ablation member involves an extruded shaft including a plurality of lumens. The shaft can be formed of Pebax or another suitably flexible thermoplastic. The shaft includes three lumens: a balloon anchor wire lumen, a fluid lumen, and an electrical lead lumen. Although the lumens are arranged in a side-by-side arrangement, two or more of the lumens can have a coaxial arrangement. Plugs close the distal ends of the electrical lead lumen and the fluid lumen.

The shaft supports the electrodes. The electrodes are spaced along the length of the shaft to define the linear ablation element. A conductor lead extends through the wall of the shaft from the electrical lead lumen at a point near the corresponding electrode. Any of the above-described connectors can be used to electrically couple an unshielded end of the conductor wire to the corresponding electrode. Each of the electrical leads is connected to the proximal coupler located at the proximal end of the tissue ablation device assembly.

The porous membrane covers the electrodes supported by extrusion shaft. A proximal end of the porous membrane is securely sealed about the outer surface of the shaft, and the distal end of the porous member is securely sealed about the shaft at a point proximal of the distal end of the shaft. The ends of the porous membrane can be attached to the shaft in any of the above-described manners.

This variation of the ablation member can also include one or more thermocouples. The thermocouples are attached to the porous membrane in the manner described above. The thermocouple wires extend through the membrane and through a hole in the shaft that opens into the electrical lead lumen, and are routed proximally through the lumen. The proximal ends of the thermal couple wires are connected to an electrical connector of a proximal coupler.

The shaft also includes an opening located just distal of the annular attachment of the proximal end of the porous member to the shaft. The opening extends from the fluid lumen and opens into an inner space defined within the porous membrane. In this manner, fluid can flow from the fluid lumen and into the inner space so as to pressurize the inner space before passing through the membrane in the manner described above.

In each of the above-described variations of the ablation member, the porous membrane covers the electrodes. The porous membrane, however, can lie inside or beneath the electrodes while still providing an even flow past each of the electrodes. This modification can be incorporated into each of the variations described above. Thus, for example, the porous membrane located between the electrodes and the braided structure. The porous membrane lies atop the braided structure. The electrodes are placed about the braided structure and the porous membrane. The ablation member desirably includes a reduced diameter section in which the electrodes reside to maintain a generally uniform profile along the distal end of the tissue ablation device assembly. Spacers can also be positioned within this section to lie between adjacent pairs of electrodes. As noted above, such spacers prevent fluid from flowing through the porous membrane at locations other than those about which an electrode is located. The ablation member, however, can be configured without spacers so as to provide a fluid flow between adjacent electrodes.

Further variations of the ablation member may include a design where the distal end of the ablation member is open; however, it desirably has a tapering diameter. The smaller diameter permits some pressure to build within the fluid passageway such that at least some of the fluid within the passageway emanates radially through the braided structure and the porous membrane, and across the electrodes. The distal end also can be rounded to ease tracking through a venous or arterial access path.

The braided structure form supports the porous membrane over its entire length. Other support can also be used. For example, internal or external rings can be spaced at various points along the length of the porous membrane to support further the membrane. In the alternative, a mandrel can also be used for this purpose. A proximal end of the mandrel can be embedded with the laminate structure and project in the distally.

Alternatively, a fluid delivery tube is located within the braided structure and can be moved by its proximal end located outside the patient, so as to vary the location of the distal end of the tube. The distal end of the tube includes one or more openings which allow fluid to be delivered by the tube into the pressurizable passageway. By moving the distal end of the fluid tube, the amount of fluid flowing across a particular electrode can be varied. To further promote this effect, the fluid tube can include baffles located on the proximal and distal sides of the fluid openings. These baffles enhance a radial flow of the fluid through porous membrane. Of course, these features can also be incorporated into several of the other variations described above.

The foregoing describes variations of an ablation member used to form linear ablations within a body space. The ablation member can be incorporated into a variety of delivery devices so as to locate and position the ablation member within the body space. At least one of the proximal and distal ends of the ablation member desirably is connected to the delivery device. That end is maneuverable within the body space by manipulating a proximal end of the delivery device.

In order to add the proper positioning of the ablation element within the porous membrane, the catheter tip and the porous membrane desirably include indicia which correspond to each other once the distal end of the ablation member has been advanced to a point positioning it within the membrane. For in vivo applications, such indicia can take the form of radiopaque markers positioned at corresponding locations on the catheter and the porous membrane (or another location on the sheath).

Linear Ablation System

Figure 9:
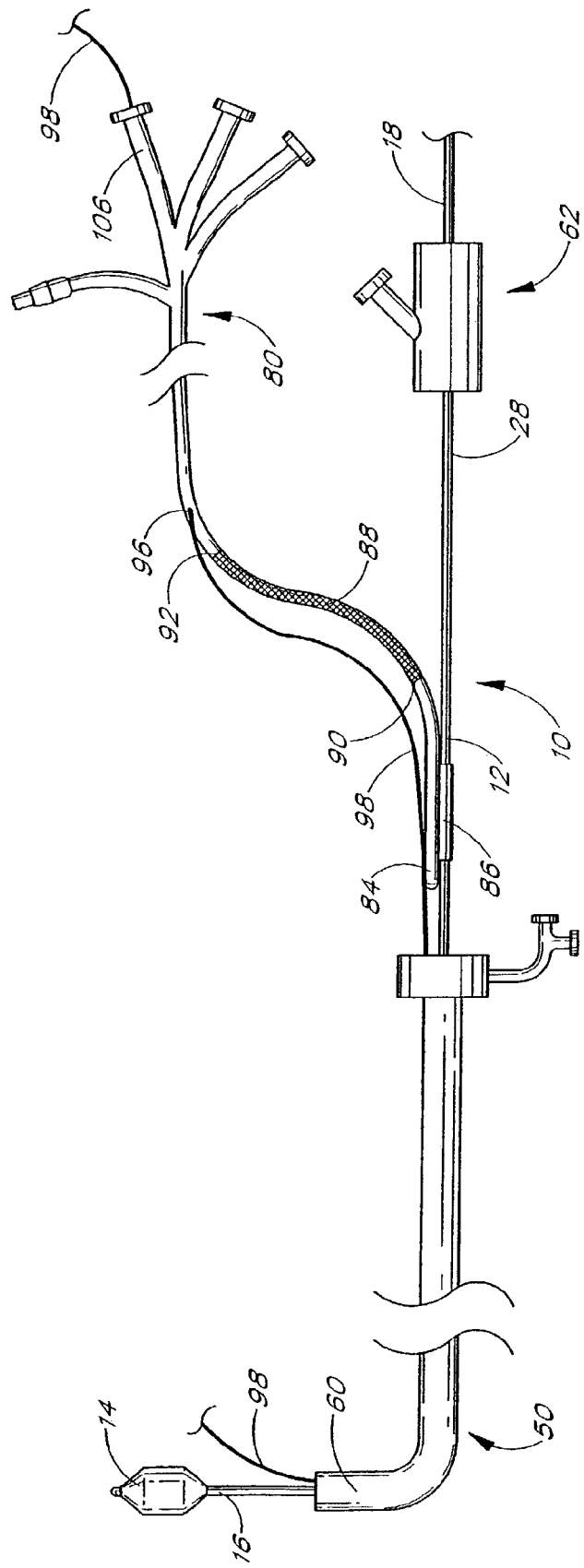
FIG. 9 is a perspective view of the guide system of the present invention, showing tracking of the distal end of the ablation catheter over the balloon anchor wire.

The linear ablation system of FIG. 9 illustrates the relationship among the transeptal sheath 50, the balloon anchor wire 10 and the ablation catheter 80, including the optional guidewire 98 for positioning the proximal end 92 of the ablation element 88. The guide member 56, described in FIGS. 6 & 7, would already have been utilized to guide the balloon catheter 10 and the guidewire 98 into the first and second pulmonary veins, respectively, and subsequently removed, as detailed below, before the system illustrated in FIG. 9 was assembled.

The balloon anchor wire 10 is shown passing through and slideably engaged within the transeptal sheath 50, wherein the distal region of the balloon anchor wire 16 having the balloon 14 is located distal to the transeptal sheath 50 and the proximal region of the balloon anchor wire having the Y-adapter 62 is located proximal to the transeptal sheath 50. The corewire 18 is shown extending proximally beyond the Y-adapter 62. A guidewire 98 also passes through the transeptal sheath 50 and is slideably engaged within the ablation catheter 80, entering the ablation catheter through a distal guidewire port 96 and extending proximally beyond the proximal guidewire port 106 of the ablation catheter 80. The tracking means 86 on the distal portion of the 84 of the ablation catheter 80 is shown slideably engaging the tubular member 12 of the balloon anchor wire 10 at a location proximal to the transeptal sheath 50.

Figure 10:
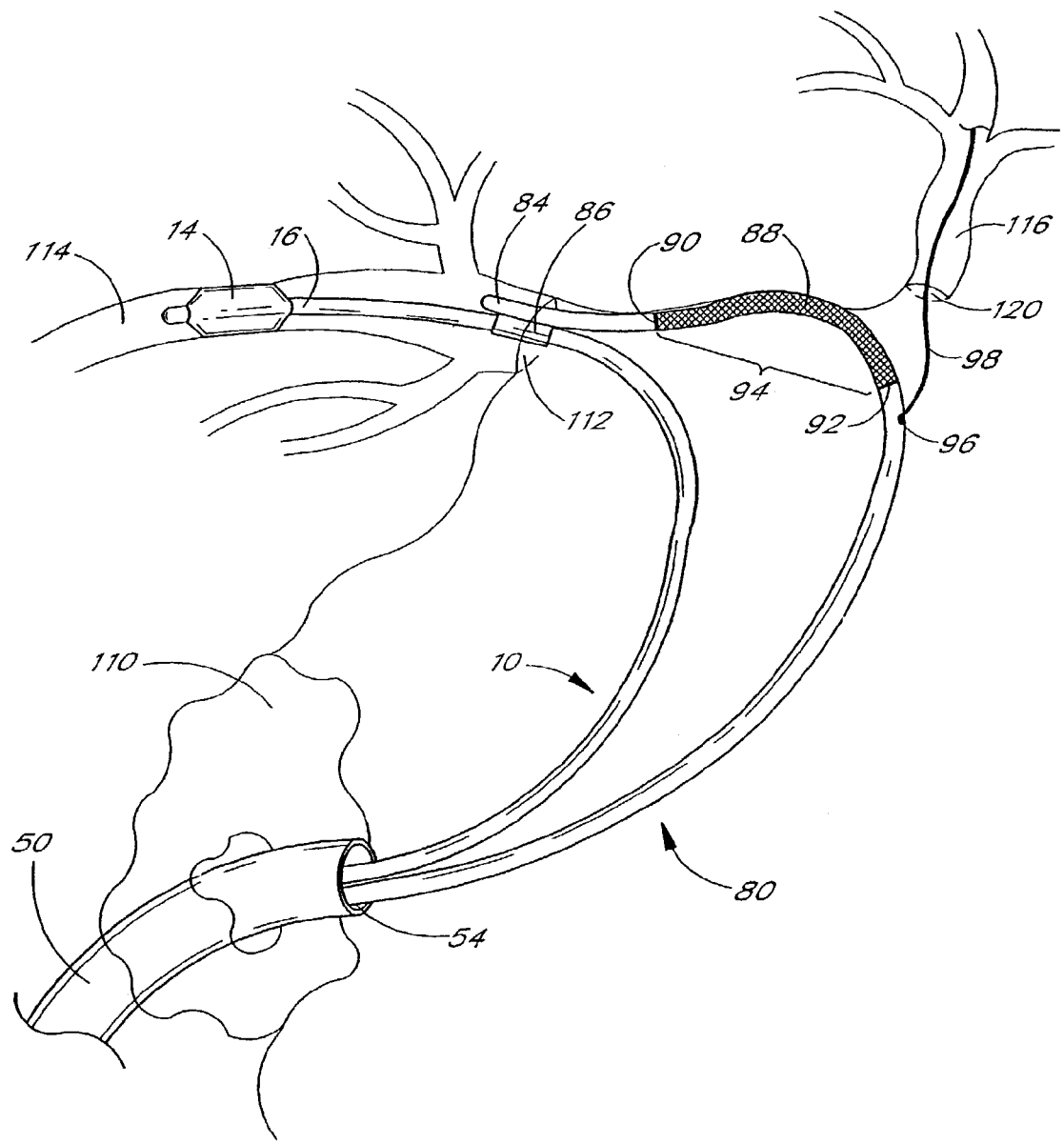
FIG. 10 is a schematic view of the proximal guidewire variation of the guide system of the present invention showing the relationship of the transeptal sheath, the balloon anchor wire, the proximal guidewire and the ablation catheter in situ.

The preferred variation of the ablation system of the present invention is shown in situ in FIG. 10. The transeptal sheath 50 traverses the atrial septum 110 that separates the right and left atria. The distal end 54 of the transeptal sheath opens into the left atrium. Emerging from the transeptal sheath and engaged therein are the balloon anchor wire 10 and the ablation catheter 80. The balloon 14 on the distal region 16 of the balloon anchor wire is shown inflated within a first pulmonary vein 114, the balloon anchor wire being thereby anchored within the first pulmonary vein. The tracking means 86 on the distal portion of the ablation catheter is shown slideably engaging and tracking along balloon anchor wire into the ostium 112 of the first pulmonary vein 114. As the ablation catheter is advanced into the first pulmonary vein 114, the distal end 90 of the ablation element 88 becomes positioned within the first ostium 112 of the first pulmonary vein 114.

The proximal end 92 of the ablation element 88 is shown being guided toward the second ostium 120 of a second pulmonary vein 116. By further advancing the ablation catheter 80 through the transeptal sheath 50 and into the left atrium, the guidewire port 96 of the ablation catheter 80 tracks along the guidewire 98 extending from the second pulmonary vein 116, thereby positioning the proximal end 92 of the ablation element within the ostium 120 of the second pulmonary vein 116. Thus, by positioning the distal end 90 of the ablation element 88 within the first ostium 112 of the first pulmonary vein using the balloon anchor wire, and the proximal end 92 of the ablation element 88 within the second ostium 120 of the second pulmonary vein using the guidewire 98, the apparatus comprising the positioning and anchoring system of the present invention is adapted to form a linear lesion along the length of tissue between the two ostia, corresponding to the ablation length 94.

Method of Making the Balloon Anchor Wire

The balloon may be blown by conventional methods from any low-density polymers or copolymers known in the art, such as polyethylene, polypropylene, polyolefins, PET, nylon, urethane, silicon, or Cflex. In a working example, the balloon was made from an irradiated linear low density polyethylene of about 0.015"/0.027" using pressurized air at about 50 psi in a hot box at about 360° F. The balloon OD ranged from about 0.050" to about 0.250" but preferably measured approximately 0.118" (3.0 mm)±0.004" at 8 atm. The working length of the balloon varied from about 4 mm to about 16 mm. Preferably, the working length measured about 10±2 mm. The shaft of the balloon had an ID ranging from about 0.010" to about 0.100", preferably about 0.030" for about 8 cm proximal and about 2 cm distal to the balloon.

To neck the proximal and distal ends of the balloon to the shaft, a heat shield was first placed against the proximal taper of the balloon. Using a hot box set at 360° F., the proximal end of the balloon was necked down onto a 0.029" OD mandrel for 10.5 cm. The region was again necked for 10 cm onto a 0.022" OD mandrel, leaving the proximal 0.5 cm at 0.029" ID. A heat shield was then placed against the distal taper of the balloon and the distal end of the balloon was necked for at least 1 cm onto a 0.018" OD mandrel. Finally, the proximal 0.029" ID segment was trimmed down to 0.4 mm and the distal necked segment was trimmed at about 3 mm distal to the balloon taper.

The tubular member may be made from any polymer known in the art. In a working example, a tubular member having an intermediate region and integral corewire, and a proximal region with no corewire (see FIG. 1B) was made. The intermediate region was constructed from a 0.025"/0.029" polyimide tube. Using a hot box set to 750° F., the distal end of the tube was necked at least 5 mm onto a 0.022" OD mandrel. The necked distal end was trimmed to 4 mm. The tube was marked at 100 cm from the necked distal end. Using the same process parameters as described above, the proximal end was necked at least 5 mm onto a 0.020" OD mandrel. The necked proximal end was trimmed to 4 mm.

The proximal segment of the tubular member was constructed from a 0.022"/0.032" polyimide tube. Using a hot box set to 750° F., the distal end was flared onto a 0.026" mandrel for 4 mm. A 0.020" mandrel was placed into the flared distal end and a 1-2 mm wide notch was made in the wall of the tube about 1 cm proximal to the flared distal end. The two shaft members were then joined. A 0.020" mandrel was inserted through the length of the intermediate region shaft for support. The necked distal end of the intermediate region shaft was inserted into the 0.029" ID proximal end of the balloon shaft. Loctite 498 adhesive was applied to the joint. The adhesive preferably wicked around the circumference of the joint. Loctite accelerator was applied as needed.

The 0.020" mandrel was removed from the intermediate segment and another 0.020" mandrel was placed through the length of the proximal tubular segment for support. The flared distal end of the 0.022"/0.032" proximal segment was slid over the necked proximal end of the 0.025"/0.029" intermediate segment. Loctite adhesive was applied to the joint, wicking around the circumference of the joint. Loctite accelerator was applied as needed.

The corewire was prepared from a 115 cm length of either 0.014" Guidant/ACS High Torque "Standard" or "Traverse" guidewire. The Teflon coating was sanded off the proximal end for 2 cm. The edge of the cut core was rounded. The wire was wiped with a solvent such as heptane to remove the silicon coating.

The corewire was bonded to the distal end of the balloon shaft by inserting the proximal end of the corewire into the distal end of the balloon and through the shaft. The core was aligned such that about 2 cm protruded beyond the distal end of the balloon. A guidewire solder joint was aligned about 1 mm distal to the end of the balloon taper. Loctite adhesive was applied to bond the distal end of the balloon to the corewire. The adhesive wicked around the circumference of the joint. Loctite accelerator was applied as needed.

A 0.009" mandrel was fed up the proximal end of the tubular member until it pushed past the proximal end of the corewire, thereby pushing the corewire against the polyimide tube in the region of the adhesive joint between the intermediate and proximal regions. The corewire was then bonded to the proximal region of the tubular member using Loctite adhesive applied through the notch which had been cut in the 0.020"/0.032" polyimide tube. The adhesive wicked approximately 2 mm in either direction. Loctite accelerator was applied as needed.

The adhesive joints were sanded to keep them below about 0.040" OD. A 0.014" ID wire coil was wound from 0.005" diameter 90 Pt/10 Ir wire, stretched to a pitch of approximately 0.010" and trimmed to about a 20 mm length. The 0.014"/0.024" coil was slid over the tip until the proximal end butts against the adhesive joint. The distal end of the outer coil was trimmed so that it was flush with an inner coil. About 1-2 mm of the coil was bonded to the end of the existing joint using Loctite 4011 adhesive and accelerator as needed. The distal end of the outer coil was soldered to the distal end of the inner coil, using a solder joint of about 1-1.5 mm.

After leak testing the assembly with air at about 70 psi, the balloon was placed in a sheath of 0.037" ID Teflon tubing. The sheathed balloon was heated in a heat box at 140° F. for about 1 minute. Dow 360 Silicon and MDX was applied to the shaft of the tubular member proximal to the balloon and allowed to cure.

Method of Using the Balloon Anchor Wire

A patient diagnosed with focal arrhythmia originating from an arrhythmogenic origin or focus in a pulmonary vein may be treated with a tissue ablation device assembly of the present invention by using the assembly to form a longitudinal conduction block along a path of the wall tissue of the pulmonary vein that either includes the arrhythmogenic origin or is between the origin and the left atrium. In the former case, the conduction block destroys the arrhythmogenic tissue at the origin as it is formed through that focus. In the latter case, the arrhythmogenic focus may still conduct abnormally, although such aberrant conduction is prevented from entering and affecting the atrial wall tissue due to the intervening longitudinal conduction block.

The ablation method of the present invention includes positioning an ablation element at an ablation region along the pulmonary vein and ablating a continuous region of tissue in the pulmonary vein wall at the ablation region.

In positioning the ablation element at the ablation region, a distal tip of a balloon anchor wire is first positioned within the left atrium according to a transeptal access method, which will be described in more detail below, and through the fossa ovalis. The right venous system is first accessed using the "Seldinger" technique, wherein a peripheral vein (such as a femoral vein), is punctured with a needle and the puncture wound is dilated with a dilator to a size sufficient to accommodate a introducer sheath. An introducer sheath that has at least one hemostatic valve is seated within the dilated puncture wound while relative hemostasis is maintained. With the introducer sheath in place, the balloon anchor wire is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intra-atrial septal wall. A "Brochenbrough" needle or trocar is then advanced distally through the guiding catheter until it punctures the fossa ovalis. A separate dilator can also be advanced with the needle through the fossa ovalis to prepare an access port through the septum for seating the transeptal sheath. Thereafter, the transeptal sheath replaces the needle across the septum and is seated in the left atrium through the fossa ovalis, thereby providing access for object devices through its own inner lumen and into the left atrium.

It is also contemplated that other left atrial access methods may be utilized for using the balloon anchor wire and tissue ablation member of the present invention. In one alternative variation, a "retrograde" approach may be used, wherein a guiding catheter is advanced into the left atrium from the arterial system. In this variation, the Seldinger technique is employed to gain vascular access into the arterial system, rather than the venous system, such as at a femoral artery. The guiding catheter is advanced retrogradely through the aorta, around the aortic arch, into the left ventricle, and then into the left atrium through the mitral valve.

After gaining access to the left atrium, a balloon anchor wire is advanced into the pulmonary vein. This is generally done through a preshaped guide which is coaxial within the transeptal sheath seated in the fossa ovalis, such as for example, the preshaped guide members described in FIGS. 6A-D, or by using one of the directional catheters disclosed in U.S. Pat. No. 5,575,766 to Swartz. Alternatively, the balloon anchor wire may have, sufficient stiffness and maneuverability in the left atrial cavity to unitarily select the desired pulmonary vein distally of the transeptal sheath seated at the fossa ovalis.

Where either of the fixed corewire variations of the balloon anchor wire shown in FIGS. 1A & B are employed, the balloon anchor wire is fed directly into the guide member. Alternatively, where the over-the-wire variation of the balloon anchor wire shown in FIG. 3 is used, the balloon anchor wire is either pre-loaded with a guidewire in the guidewire passageway of the tubular member before being inserted into the guide member or a guidewire alone is fed through the guide member and into the first pulmonary vein and then the tubular member is fed over the guidewire and into the guide member. In either case, a negative pressure is applied to the balloon to insure that it is maintained in a radially collapsed state. The balloon anchor wire is advanced through the guide member until the balloon exits the shaped distal end of the guide member, the balloon anchor wire being aimed by the guide member toward the first pulmonary vein.

The balloon anchor wire is then advanced into the first pulmonary vein to a suitable anchoring position. The fixed corewire variation of the balloon anchor wire is directly advanced into the first pulmonary vein. Alternatively, where the over-the-wire variation is used, the guidewire is advanced into the pulmonary vein first and then the tubular member with the distal balloon follows, tracking over the guidewire and into the pulmonary vein. Anchoring of the catheter is accomplished in either case by inflating the balloon to a predetermined air pressure or volume of a saline/contrast mixture. Effective anchoring is tested by gently tugging on the balloon anchor wire. If the anchor wire is not sufficiently anchored, negative pressure is again applied to deflate the balloon and the anchor wire is advanced further into the pulmonary vein or one of its branches. Inflating, testing and repositioning are performed in this manner until the balloon anchor wire is sufficiently anchored. If necessary the anchor wire may be advanced into a different branch of the first pulmonary vein to find a secure anchoring position.

Once the balloon anchor wire is securely anchored, the shaped guide member may be retracted back through the transeptal sheath and removed. The method of removing the guide member will vary depending on the design of the balloon anchor wire and the guide member. In one variation, the guide member may be designed to peel away from the balloon anchor wire. Alternatively, where the proximal end of the balloon anchor wire has a removable Y-adapter (inflation/deflation hub), the Y-adapter is removed by releasing the pressure on the balloon, loosening the distal and proximal O-ring knobs on the adapter, and sliding the adapter off the balloon anchor wire. Care must be taken not to displace the balloon on the distal end of the anchor wire when removing the adapter from the proximal end of the anchor wire. Once the Y-adapter has been removed, the guide member may be withdrawn completely by sliding it off the proximal end of the balloon anchor wire.

The ablation catheter, which is adapted to slideably engage the balloon anchor wire, is then slid over the proximal end of the balloon anchor wire. The ablation catheter has an ablation element with an ablation length that extends proximally from the distal end portion of the ablation catheter, the ablation length being defined by distal and proximal ends of the ablation element. Where the optional guidewire is being employed for positioning the proximal portion of the ablation element within a second pulmonary vein ostium, the ablation catheter is further adapted to slideably engage the guidewire within a guidewire lumen incorporated into the ablation catheter, the distal opening of the guidewire lumen being located proximal to the proximal end of the ablation element. Once the ablation catheter is advanced past the proximal end of the balloon anchor wire, the Y-adapter is reattached and the balloon is reinflated. The user should gently tug on the balloon anchor wire to insure that it is still securely anchored in the first pulmonary vein.

The ablation catheter is then advanced over the balloon anchor wire, through the transeptal sheath, and continuing until the distal end of the ablation catheter, including the distal end of the ablation element, engages the first pulmonary vein ostium. A combination of pushing and pulling alternatively on both the balloon anchor wire and the ablation catheter may be employed to facilitate advancement of the ablation catheter. In a variation of the method, a stylet may be placed inside the ablation catheter to further assist in advancing it along the balloon anchor wire toward the first pulmonary vein ostium. Once the distal end of the ablation catheter engages the first pulmonary vein ostium and is securely seated therein, the proximal portions of the ablation catheter, including the proximal end of the ablation element, are further advanced into the left atrium, causing the ablation catheter to prolapse against the atrial wall. If a stylet was used inside the ablation catheter to facilitate advancement and positioning of the ablation catheter, retracting the stylet now may permit the catheter to conform more readily to the atrial wall.

Where the optional guidewire is being employed to facilitate positioning of the proximal end of the ablation element, the guidewire is advanced into a second pulmonary vein prior to prolapsing the ablation catheter against the atrial wall. Once the guidewire is in place within the second pulmonary vein, the proximal end of the ablation element is advanced more accurately toward the second pulmonary vein ostium by tracking along the guidewire.

Delivery of RF energy to the endocardial tissue of the pulmonary vein is commenced once the ablation member is positioned at the desired ablation region. Good contact between the ablation element and the underlying tissue facilitates the creation of a continuous transmural lesion. RF energy from the ablation actuator is delivered to electrodes via electrical leads. The ablation actuator desirably includes a current source for supplying an RF current, a monitoring circuit, and a control circuit. The current source is coupled to the linear ablation element via a lead set, and to a ground patch. The monitor circuit desirably communicates with one or more sensors (e.g., temperature or current sensors) which monitor the operation of the linear ablation element. The control circuit is connected to the monitoring circuit and to the current source in order to adjust the output level of the current driving the electrodes of the linear ablation element based upon the sensed condition (e.g., upon the relationship between the monitored temperature and a predetermined temperature set point).

At the same time, conductive fluid, such as saline, is directed into the fluid coupler and through the fluid lumen. In some instances, it may be desirable to begin to apply positive fluid pressure even before RF ablation is commenced in order to prevent blood accumulation in or on the ablation member.

In one variation, the saline passes through openings in the fluid tubing to an inner space within the porous membrane. When the pressure within the inner space reaches a predetermined pressure, the fluid weeps out of the porous membrane. The fluid can be uniformly distributed along the longitudinal length of the ablation element because the fluid does not immediately flow through the porous membrane, but instead remains within the inner space until the predetermined pressure is reached. This provides for both a uniform flow of fluid through the length of the porous membrane and a uniform flow of RF energy along the ablation element. That is, the porous membrane diffuses the saline across each individual electrode, as well as across the array of electrodes. While the conductive fluid or saline is used to create a uniform conductive path between the electrodes and the target tissue, the saline can be alternatively or additionally utilized to cool the ablation electrodes. The fluid flows both through the helical coil of the ablation element and between the plurality of ablation elements of the ablation member, thereby facilitating the cooling of the electrodes by the fluid. The bath of saline may possibly cool the electrodes so as to be capable of delivering high levels of current or be capable of longer durations to produce deeper lesions.

Once a lesion has been formed at the target spot, the guiding catheter may be repositioned and additional lesions formed.

An ablation member for use in forming a circumferential lesion, in accordance with another aspect of the present invention may take the form of annular ultrasonic transducer. The annular ultrasonic transducer has a unitary cylindrical shape with a hollow interior (i.e., is tubular shaped); however, the transducer applicator can have a generally annular shape and be formed of a plurality of segments. For instance, the transducer applicator can be formed by a plurality of tube sectors that together form an annular shape. The tube sectors can also be of sufficient arc lengths so as when joined together, the sectors assembly forms a "clover-leaf" shape. This shape is believed to provide overlap in heated regions between adjacent elements. The generally annular shape can also be formed by a plurality of planar transducer segments that are arranged in a polygon shape (e.g., hexagon). In addition, although in the illustrated embodiment the ultrasonic transducer comprises a single transducer element, the transducer applicator can be formed of a multi-element array, as described in greater detail below.

The cylindrical ultrasound transducer may include a tubular wall that includes three concentric tubular layers. The central layer is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members enclose a central layer within their coaxial space and are constructed of an electrically conductive material. These transducer electrodes comprise a metallic coating, and more preferably a coating of nickel, copper, silver, gold, platinum, or alloys of these metals.

One more detailed construction for a cylindrical ultrasound transducer for use in the present application is as follows. The length of the transducer or transducer assembly (e.g., multi-element array of transducer elements) desirably is selected for a given clinical application. In connection with forming circumferential condition blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. The positioning of the transducer within an inflatable member, e.g., a balloon, may be desirable for facilitating the positioning of the transducer within a pulmonary vein or pulmonary vein ostium at a suitable distance for delivering a circumferential lesion. The transducer preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by an outer balloon for up to about 2 cm outer diameter of the balloon. For applications in other body spaces, the transducer applicator may have an outer diameter within the range of about 1 mm to greater than 3-4 mm (e.g., as large as 1 to 2 cm for applications in some body spaces).

The central layer of the transducer has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer is vibrated across the wall thickness and to radiate collimated acoustic energy in the radial direction. For this purpose, the distal ends of electrical leads are electrically coupled to outer and inner tubular members or electrodes, respectively, of the transducer, such as, for example, by soldering the leads to the metallic coatings or by resistance welding. The electrical leads are 4-8 mil (0.004 to 0.008 inch diameter) silver wire or the like.

The proximal ends of these leads are adapted to couple to an ultrasonic driver or actuator. The leads may be separate wires within an electrical lead lumen, in which configuration the leads must be well insulated when in close contact. Other configurations for leads are therefore contemplated. For example, a coaxial cable may provide one cable for both leads which is well insulated as to inductance interference. Or, the leads may be communicated toward the distal end portion of the elongate body through different lumens that are separated by the catheter body.

The transducer also can be sectored by scoring or notching the outer transducer electrode and part of the central layer along lines parallel to the longitudinal axis L of the transducer. A separate electrical lead connects to each sector in order to couple the sector to a dedicated power control that individually excites the corresponding transducer sector. By controlling the driving power and operating frequency to each individual sector, the ultrasonic driver can enhance the uniformity of the ultrasonic beam around the transducer, as well as can vary the degree of heating (i.e., lesion control) in the angular dimension.

The ultrasound transducer just described is combined with the overall device assembly according to the present embodiment as follows. In assembly, the transducer desirably is "air-backed" to produce more energy and to enhance energy distribution uniformity, as known in the art. In other words, the inner member does not contact an appreciable amount of the inner surface of transducer inner tubular member. This is because the piezoelectric crystal which forms central layer of ultrasound transducer is adapted to radially contract and expand (or radially "vibrate") when an alternating current is applied from a current source and across the outer and inner tubular electrodes of the crystal via the electrical leads. This controlled vibration emits the ultrasonic energy that is adapted to ablate tissue and form a circumferential conduction block according to the present embodiment. Therefore, it is believed that appreciable levels of contact along the surface of the crystal may provide a dampening effect that would diminish the vibration of the crystal and thus limit the efficiency of ultrasound transmission.

For this purpose, the transducer seats coaxial about the inner member and is supported about the inner member in a manner providing a gap between the inner member and the transducer inner tubular member. That is, the inner tubular member forms an interior bore that loosely receives the inner member. Any of a variety of structures can be used to support the transducer about the inner member. For instance, spacers or splines can be used to coaxially position the transducer about the inner member while leaving a generally annular space between these components. In the alternative, other conventional and known approaches to support the transducer can also be used. For instance, O-rings that circumscribe the inner member and lie between the inner member and the transducer can support the transducer. More detailed examples of the alternative transducer support structures just described are disclosed in U.S. Pat. No. 5,620,479 to Diederich, issued Apr. 15, 1997, and entitled "Method and Apparatus for Thermal Therapy of Tumors," and U.S. Pat. No. 5,606,974 to Castellano, issued Mar. 4, 1997, and entitled "Catheter Having Ultrasonic Device." The disclosures of these references are herein incorporated in their entirety by reference thereto.

In one embodiment, a stand-off is provided in order to ensure that the transducer has a radial separation from the inner member to form a gap filled with air and/or other fluid. In one preferred mode, the stand-off is a tubular member with a plurality of circumferentially spaced outer splines which hold the majority of the transducer inner surface away from the surface of the stand-off between the splines, thereby minimizing dampening affects from the coupling of the transducer to the catheter. The tubular member which forms a stand-off may also provide its inner bore as the guidewire lumen in the region of the ultrasound transducer, in the alternative to providing a separate stand-off coaxially over another tubular member which forms the inner member.

In a further mode, the elongate body can also include additional lumens that lie either side-by-side to or coaxial with the guidewire lumen and which terminate at ports located within the space between the inner member and the transducer. A cooling medium can circulate through space defined by the stand-off between the inner member and the transducer via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer desirably is electrically and mechanically isolated from the interior of the balloon. Any of a variety of coatings, sheaths, sealants, tubings and the like may be suitable for this purpose, such as those described in U.S. Pat. Nos. 5,620,479 and 5,606,974. A conventional, flexible, acoustically compatible, and medical grade epoxy is applied over the transducer. The epoxy may be, for example, Epotek 301, Epotek 310, which is available commercially from Epoxy Technology, or Tracon FDA-8. In addition, a conventional sealant, such as, for example, General Electric Silicon II gasket glue and sealant, desirably is applied at the proximal and distal ends of the transducer around the exposed portions of the inner member, wires, and stand-off to seal the space between the transducer and the inner member at these locations.

An ultra thin-walled polyester heat shrink tubing or the like then seals the epoxy coated transducer. Alternatively, the epoxy covered transducer, inner member and stand-off can be instead inserted into a tight thin wall rubber or plastic tubing made from a material such as Teflon(g, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy-coated transducer. As the tube shrinks, excess epoxy flows out and a thin layer of epoxy remains between the transducer and the heat shrink tubing. These layers protect the transducer surface, help acoustically match the transducer to the load, makes the ablation device more robust, and ensures air-tight integrity of the air backing.

The tubing extends beyond the ends of transducer and surrounds a portion of the inner member on either side of the transducer. A filler can also be used to support the ends of the tubing. Suitable fillers include flexible materials such as, for example, but without limitation, epoxy, Teflon® tape and the like.

The ultrasonic actuator generates alternating current to power the transducer. The ultrasonic actuator drives the transducer at frequencies within the range of about 5 to about 20 MHz, and preferably within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator can drive the transducer at frequencies within the range of 6.8 MHz and 7.2 MHz by continuously or discretely sweeping between these frequencies.

Figure 11:
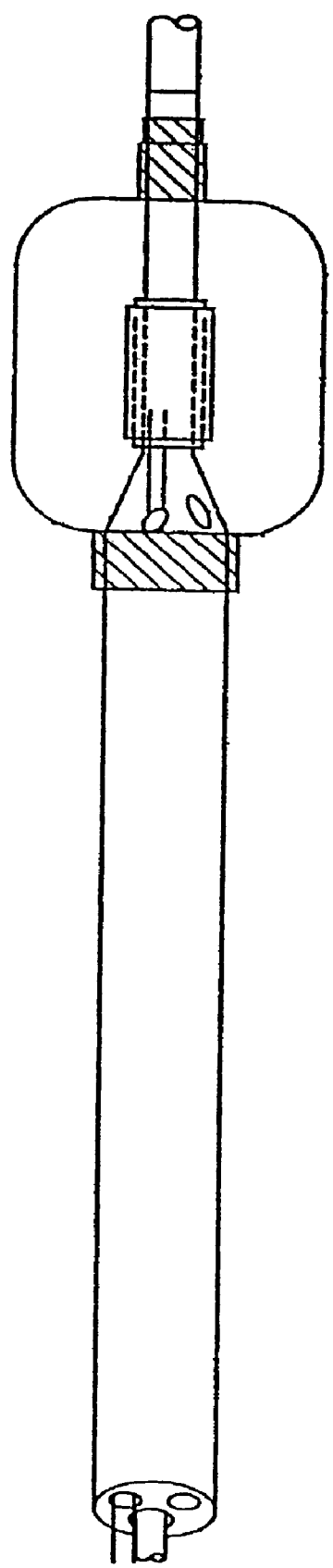
FIG. 11 is a longitudinal cross-sectional view of an anchor device in accordance with a preferred mode of the present invention, showing an over-the-wire catheter with an ultrasound ablation element positioned along the distal end portion within an expandable member.

The ultrasound transducer of the present embodiment sonically couples with the outer skin of the balloon in a manner that forms a circumferential conduction block in a pulmonary vein as follows. FIG. 11 shows an ablation catheter in accordance with this mode of the present invention. An ultrasound transducer is located along the distal end portion of the catheter shaft within an inflatable balloon. Initially, the ultrasound transducer is believed to emit its energy in a circumferential pattern that is highly collimated along the transducer's length relative to its longitudinal axis L. The circumferential band therefore maintains its width and circumferential pattern over an appreciable range of diameters away from the source at the transducer. Also, the balloon is preferably inflated with fluid that is relatively ultrasonically transparent, such as, for example, degassed water. Therefore, by actuating the transducer while the balloon is inflated, the circumferential band of energy is allowed to translate through the inflation fluid and ultimately sonically couple with a circumferential band of balloon skin which circumscribes the balloon. Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

In one particular balloon-transducer combination, the ultrasound transducer preferably has a length such that the ultrasonically coupled band of the balloon skin, having a similar length d according to the collimated electrical signal, is shorter than the working length D of the balloon. According to this aspect of the relationship, the transducer is adapted as a circumferential ablation member, which is coupled to the balloon to form an ablation element along a circumferential band of the balloon, therefore forming a circumferential ablation element band that circumscribes the balloon. Preferably, the transducer has a length that is less than two-thirds the working length of the balloon, and more preferably is less than one-half the working length of the balloon. By sizing the ultrasonic transducer length d smaller than the working length D of the balloon—and hence shorter than a longitudinal length of the engagement area between the balloon and the wall of the body space (e.g., pulmonary vein ostium)—and by generally centering the transducer within the balloon's working length D, the transducer operates in a field isolated from the blood pool. A generally equatorial position of the transducer relative to the ends of the balloon's working length also assists in the isolation of the transducer from the blood pool. It is believed that the transducer placement according to this arrangement may be preventative of thrombus formation that might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate body may include an additional radiopaque marker or markers to identify the location of the ultrasonic transducer in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The radiopaque marker is positioned coaxially over an inner tubular member.

The present circumferential ablation device may be introduced into a pulmonary vein of the left atrium in a manner similar to that described above. The circumferential ablation element may be positioned as described for the linear ablation element, by tracking along the balloon anchor wire of the present invention. In one embodiment, the circumferential ablation element may be placed within the balloon of the balloon anchor wire, so as to ablate a circumferential region of the pulmonary vein. In a preferred embodiment, the ablation device may include both circumferential and linear ablation elements. Once properly positioned within the pulmonary vein or vein ostium, the pressurized fluid source inflates the balloon to engage the lumenal surface of the pulmonary vein ostium. Once properly positioned, the ultrasonic driver is energized to drive the transducer. It is believed that by driving the ultrasonic transducer at 20 acoustical watts at an operating frequency of 7 megahertz, that a sufficiently sized lesion can be formed circumferentially about the pulmonary vein ostium in a relatively short period of time (e.g., 1 to 2 minutes or less).

It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

In an alternative embodiment of the present invention, the balloon may have a "straight" configuration with a working length D and a relatively constant diameter between proximal and distal tapers. This variation is believed to be particularly well adapted for use in forming a circumferential conduction block along a circumferential path of tissue that circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon.

The balloon is also concentrically positioned relative to the longitudinal axis of the elongate body. It is understood, however, that the balloon can be asymmetrically positioned on the elongate body, and that the ablation device can include more than one balloon.

Another assembly according to the invention includes a balloon that has a tapered outer diameter from a proximal outer diameter $X_1$ to a smaller distal outer diameter $X_2$. According to this mode, this tapered shape is believed to conform well to other tapering regions of space, and may also be particularly beneficial for use in engaging and ablating circumferential paths of tissue along a pulmonary vein ostium.

A similar shape for the balloon includes a bulbous proximal end. In this embodiment, the proximate bulbous end of the central region gives the balloon a "pear"-shape. More specifically, a contoured surface is positioned along the tapered working length L and between proximal shoulder and the smaller distal shoulder of balloon. This pear shaped embodiment is believed to be beneficial for forming the circumferential conduction block along a circumferential path of atrial wall tissue that surrounds and perhaps includes the pulmonary vein ostium. Circumferential lesion electrically isolates the respective pulmonary vein from a substantial portion of the left atrial wall. The device is also believed to be suited to form an elongate lesion which extends along a substantial portion of the pulmonary vein ostium, e.g., between the proximal edge of the lesion and the dashed line which marks a distal edge of such an exemplary elongate lesion.

As mentioned above, the transducer can be formed of an array of multiple transducer elements that are arranged in series and coaxial. The transducer can also be formed to have a plurality of longitudinal sectors. These modes of the transducer have particular utility in connection with the tapering balloon designs. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device can also include additional mechanisms to control the depth of heating. For instance, the elongate body can include an additional lumen that is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer may be mounted on a torquible member which is movably engaged within a lumen that is formed by the elongate body.

In another aspect of the balloon-transducer relationship, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape).

More particularly, the balloon includes a filter which has a predetermined pattern along the balloon surface and which is adapted to shield tissue from the ultrasound signal, for example, by either absorbing or reflecting the ultrasound signal. The filter is patterned so that the energy band which is passed through the balloon wall is substantially more narrow than the band which emits from the transducer internally of the balloon. The filter can be constructed, for example, by coating the balloon with an ultrasonically reflective material, such as with a metal, or with an ultrasonically absorbent material, such as with a polyurethane elastomer. Or, the filter can be formed by varying the balloon's wall thickness such that a circumferential band, which is narrow in the longitudinal direction as compared to the length of the balloon, is also thinner (in a radial direction) than the surrounding regions, thereby preferentially allowing signals to pass through the band. The thicker walls of the balloon on either side of the band inhibit propagation of the ultrasonic energy through the balloon skin at these locations.

For various reasons, the "narrow pass filter" embodiment may be particularly well suited for use in forming circumferential conduction blocks in left atrial wall and pulmonary vein tissues according to the present invention. It is believed that the efficiency of ultrasound transmission from a piezoelectric transducer is limited by the length of the transducer, which limitations are further believed to be a function of the wavelength of the emitted signal. Thus, for some applications a transducer may be required to be longer than the length that is desired for the lesion to be formed. Many procedures intending to form conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length which is much longer and may create lesions which are much wider than is functionally required for the block. A "narrow pass" filter along the balloon provides one solution to such competing interests.

Another variation of the balloon-transducer relationship involves placement of an ultrasonically absorbent band along the balloon and directly in the central region of the emitted energy signal from transducer. According to this variation, the ultrasonically absorbent band is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, the ultrasonically absorbent band may operate as an energy sink as an aid to control the extent of ablation to a less traumatic and invasive level than would be reached by allowing the raw ultrasound energy to couple directly to the tissue. In other words, by heating the absorbent band the signal is diminished to a level that might have a more controlled depth of tissue ablation. Further to this aspect, the absorbent band may therefore also have a width that is more commensurate with the length of the transducer.

Generally, the aforementioned ultrasonic transducers had an annular shape so as to emit ultrasonic energy around the entire circumference of the balloon. The circumferential ablation device, however, can emit a collimated beam of ultrasonic energy in a specific angular exposure. For instance, the transducer can be configured to have only a single active sector (e.g., 180 degree exposure). The transducer can also have a planar shape. By rotating the elongate body, the transducer can be swept through 360 degrees in order to form a circumferential ablation. For this purpose, the transducer may be mounted on a torquible member, in the manner described above.

Another type of ultrasonic transducer that can be mounted to a torquible member within the balloon is formed by curvilinear section and is mounted on the inner member with its concave surface facing in a radially outward direction. The inner member desirably is formed with recess that substantially matches a portion of the concave surface of the transducer. The inner member also includes longitudinal ridges on the edges of the recess that support the transducer above the inner member such that an air gap is formed between the transducer and the inner member. In this manner, the transducer is "air-backed." This spaced is sealed and closed in the manner described above.

The inverted transducer section produces a highly directional beam pattern. By sweeping the transducer through 360 degrees of rotation, as described above, a circumferential lesion can be formed while using less power than would be required with a planar or tubular transducer.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the embodiments variously shown to be "guidewire" tracking variations for delivery into a left atrium and around or within a pulmonary vein may be modified to instead incorporate a deflectable/steerable tip instead of guidewire tracking and are also contemplated. Moreover, all assemblies described are believed useful when modified to treat other tissues in the body, in particular other regions of the heart, such as the coronary sinus and surrounding areas. Further, the disclosed assemblies may be useful in treating other conditions, wherein aberrant electrical conduction may be implicated, such as for example, heart flutter. Indeed, other conditions wherein catheter-based, directed tissue ablation may be indicated, such as for example, in the ablation of fallopian tube cysts. Accordingly, it should be understood that various applications, modifications and substitutions may be made of equivalents without departing from the spirit of the invention or the scope of the following claims.

What is claimed is:

1. A method of ablating a region of tissue at a location where a pulmonary vein extends from an atrium, comprising:

inserting a transeptal sheath through an atrial septum that separates a right atrium from the left atrium;

inserting a guide member having a preshaped distal portion with a predetermined shape and a lumen in at least the preshaped distal portion through the transeptal sheath from the right atrium into the left atrium whereby the guide member takes the predetermined shape automatically external to the transeptal sheath;

pointing the preshaped distal portion of the guide member towards a predetermined pulmonary vein by adjustably advancing the guide member through the transeptal sheath, controlling the shape of the preshaped distal portion;

after advancing the guide member, slidably advancing an anchor device through the lumen of the guide member and into the atrium, the anchor device being adapted to be positioned within the pulmonary vein and having an elongate body with a proximal end portion and a distal end portion, and also having an expandable member along the distal end portion adjustable between a radially collapsed condition and a radially expanded condition that is adapted to engage the pulmonary vein;

positioning the anchor device within the pulmonary vein;

anchoring the distal end portion of the anchor device within the pulmonary vein by adjusting the expandable member from the radially collapsed condition to the radially expanded condition;

providing an ablation catheter adapted to slideably engage and track over the anchor device and also having an ablation element adapted to couple to an ablation actuator;

advancing the ablation catheter into the atrium over the anchor device until the ablation element is positioned at the location;

actuating the ablation actuator to energize the ablation element; and ablating the region of tissue with the ablation element.

2. The method of claim 1, wherein prior to advancing the ablation catheter over the anchor device, the guide member is removed.

* * * * *